United States Patent
Steidler et al.

(10) Patent No.: US 6,746,671 B2
(45) Date of Patent: Jun. 8, 2004

(54) USE OF A CYTOKINE-PRODUCING LACTOCOCCUS STRAIN TO TREAT COLITIS

(75) Inventors: Lothar Steidler, Lokeren (BE); Erik R. Remaut, Vinderhouse (BE); Walter Fiers, Destelbergen (BE)

(73) Assignee: Vlaams Interuniversitair Instituut voor Biotechnologie VZW, Zwijnaarde (BE)

( * ) Notice: Subject to any disclaimer, the term of this patent is extended or adjusted under 35 U.S.C. 154(b) by 0 days.

(21) Appl. No.: 09/838,718

(22) Filed: Apr. 19, 2001

(65) Prior Publication Data

US 2002/0019043 A1 Feb. 14, 2002

Related U.S. Application Data

(63) Continuation of application No. PCT/EP99/07800, filed on Oct. 6, 1999.

(30) Foreign Application Priority Data

Oct. 20, 1998 (EP) .............................. 98203529

(51) Int. Cl.$^7$ .......................... A01N 63/00; A61K 48/00
(52) U.S. Cl. ................... 424/93.2; 435/252.3; 435/471; 435/243; 424/93.4
(58) Field of Search ............... 424/93.2, 93.4, 424/184.1; 435/243, 471, 252.1, 252.3, 252.31, 461; 514/44

(56) References Cited

U.S. PATENT DOCUMENTS

6,262,119 B1 * 7/2001 Ferrante et al. ............. 514/560

FOREIGN PATENT DOCUMENTS

| WO | WO 96/11277 | * | 4/1996 |
| WO | WO 97/14806 | | 4/1997 |
| WO | WO 00/23471 | | 4/2000 |

OTHER PUBLICATIONS

Herfarth et al., Interleukin 10 suppresses experimental chronic, granulomatous inflammation induced by bacterial cell wall polymers, 1996, GUT, vol. 39, pp. 836–845.*
Barbara et al., interleukin 10 gene transfer prevents experimental colitis in rats, 2000, GUT, vol. 46, pp. 344–349.*
Bellini, et al., Production processes of recombinant IL–1beta from bacillus subtilis: comparison between intracellular and exocellular expression, 1991, Journal of Biotechnology, vol. 18, pp. 177–192.*
Kuby, Cytokine receptors, 1994, Immunology, pp. 304–306.*
Pouwels et al., Genetics of lactobacilli: plasmids and gene expression, 1993, Antonie Van Leeuwenhoek, vol. 64, pp: 85–107.*
Targan et al., Clarifying the causes of Croh's, 1995, Nature Medicine, vol. 1, pp. 1241–1243.*
Papadakis et al., Role of cytokine in the pathogenesis of inflammatory bowel disease, 2000, Annu. Rev. Med., vol. 51, pp. 289–298.*
Korelitz et al., Immunosuppressive therapy of inflammatory bowel disease: A historical perspective.*
Leach et al., The role of IL–10 in inflammatory bowel disease: "Of mice and men", 1999, Toxicologic Pathology, pp. 123–133.*
Page et al., Innovations in oral gene delivery: challenges and potentials, 2001, DDT, vol. 6, pp. 92–101.*
Verma et al., Gene therapy–promises; problems and prospects, 1997, Nature, vol. 389, pp. 239–242.*
McGluskie et al., Route and method of delivery of DNA vaccine influence immune responses in mice and non–human primates, 1999, Molecular Medicine, vol. 5, pp. 287–300.*
Anderson, Human gene therapy, 1998, Nature, vol. 392, pp.*
Merriam–Webster's Collegiate Dictionary, Tenth Edition, Springfield, Massachusetts, USA, 2001, p. 922.*
Steidler et al., "Mucosal Delivery of Murine Interleukin–2 (IL–2) and IL–6 by Recombinant Strains of Lactococcus lactis Coexpressing Antigen and Cytokine", *Infection and Immunity*, vol. 66, No. 7, pp. 3183–3189, Jul. 1998.
Steidler et al., "Treatment of Murine Colitis by Lactococcus lactis Secreting Interleukin–10", *Science,* vol. 289, pp. 1352–1355, Aug. 25, 2000.

* cited by examiner

*Primary Examiner*—Scott D. Priebe
*Assistant Examiner*—Brian Whiteman
(74) *Attorney, Agent, or Firm*—TraskBritt

(57) ABSTRACT

An administration strategy for the delivery at the intestinal mucosa of cytokines or cytokine antagonists, preferably of acid sensitive anti-inflammatory agents, for example, IL10 and/or soluble TNF receptor via the oral route. Preferably, inoculation occurs along with a suspension of recombinant *Lactococcus lactis* cells, which had been engineered to produce the respective proteins.

14 Claims, 11 Drawing Sheets

DSS colitis

USE OF A CYTOKINE-PRODUCING LACTOCOCCUS STRAIN TO TREAT COLITIS

CROSS-REFERENCE TO RELATED APPLICATIONS

This application is a continuation of application PCT/EP99/07800 filed Oct. 16, 1999, published in English on Apr. 22, 2000 as WO 00/23471, designating the United States of America, which itself claims priority from European Patent Application EP 98203529.7, filed on Oct. 20, 1998.

TECHNICAL FIELD

The invention relates generally to medicine, and particularly to an administration strategy for delivering cytokines or cytokine antagonists at the intestinal mucosa. Preferably, the cytokines or cytokine antagonists are acid sensitive anti-inflammatory agents, such as IL10 and/or soluble TNF receptor. These antagonists may be delivered via an oral route. Preferably, inoculation occurs along with a suspension of recombinant *Lactococcus lactis* cells that are engineered to produce the respective proteins.

BACKGROUND

The mammalian immune system is diverse and complex, and includes natural and adaptive immune mechanisms and reactions. The immune system is often described in terms of either "humoral" or "cellular immune" responses. Humoral immunity refers broadly to antibody production and actions by B-cells, while cellular immunity is mediated by cells including T-cells, dendritic cells, neutrophils, monocytes and macrophages. T-cells and B-cells are two categories of lymphocytes.

One of the mechanisms by which the immune system normally acts and regulates itself includes the production of so-called "cytokines". Cytokines mediate several positive and negative immune responses. Cytokines normally act by binding to a receptor on a target cell. The activity of cytokines can be interfered with in several ways, for example by administration of soluble receptors (extracellular domains of the receptor) or by cytokine analogues or derivatives.

IL-10 is a cytokine capable of mediating a number of actions and/or effects. It is known that IL-10 is involved in controlling the immune responses of different classes or subsets of Th cells (T-helper cells).

Inflammatory bowel disease ("IBD") refers to a group of gastrointestinal disorders characterized by a chronic non-specific inflammation of portions of the gastrointestinal tract. Ulcerative colitis ("UC") and Crohn's Disease ("CD") are the most prominent examples of IBD in humans. They are associated with many symptoms and complications, including growth retardation in children, rectal prolapse, blood in stools (e.g., melena and/or hematochezia), wasting, iron deficiency, and anemia, for example, iron deficiency anemia and anemia of chronic disease or of chronic inflammation. The etiology or etiologies of IBD are unclear. Reference hereto is made in Wyngaarden and Smith (eds.) *Cecil's Textbook of Medicine* (W. B. Saunders Co. 1985), Berkow (ed.) *The Merck Manual of Diagnosis and Therapy* (Merck Sharp & Dohme Research Laboratories, 1982), and *Harrison's Principles of Internal Medicine*, 12th Ed., McGraw-Hill, Inc. (1991).

The incidence of IBD varies greatly with geographic location. A collaborative study was commenced in Europe. It illustrated an incidence of 10.4 per 100,000 for UC and of 5.6 per 100,000 for CD, with 40% and 80% respectively higher incidences for UC and CD in northern centres when compared to those in the south. As both UC and CD are long time afflictions, they correspond-to real disturbances in the quality of life. Crohn's disease has a bimodal age distribution of onset, showing striking peaks in incidence at 20 and at 50 years of age. A higher incidence and more grievous disease profile is associated with those that peak at a younger-age. This makes CD especially poignant as afflicted adolescents and young adults are virtually deprived of the high expectations of life particularly associated with this age group.

Ulcerative colitis refers to a chronic, nonspecific, inflammatory, and ulcerative disease having manifestations primarily in the colonic mucosa. It is frequently characterized by bloody diarrhea, abdominal cramps, blood and mucus in the stools, malaise, fever, anemia, anorexia, weight loss, leukocytosis, hypoalbuminemia, and an elevated erythrocyte sedimentation rate ("ESR"). Complications can include hemorrhage, toxic colitis, toxic megacolon, occasional rectovaginal fistulas, and an increased risk for the development of colon cancer.

Ulcerative colitis is also associated with noncolon complications, such as arthritis, ankylosing spondylitis, sacroileitis, posterior uveitis, erythema nodosum, pyoderma gangrenosum, and episcleritis. Treatment varies considerably with the severity and duration of the disease. For instance, fluid therapy to prevent dehydration and electrolyte imbalance is frequently indicated in a severe attack. Additionally, special dietary measures are sometimes useful. Medications include various corticosteroids, sulphasalazine and some of its derivatives, and possibly immunosuppressive drugs.

Crohn's Disease shares many features in common with ulcerative colitis. Crohn's Disease is distinguishable in that lesions tend to be sharplydemarcated from adjacent normal bowel, in contrast to the lesions of ulcerative colitis which are fairly diffuse. Crohn's Disease predominately afflicts the ileum (ileitis) and the ileum and colon (ileocolitis). In some cases, the colon alone is diseased (granulomatous colitis) and sometimes the entire small bowel is involved (jejunoileitis). In rare cases, the stomach, duodenum, or esophagus are involved. Lesions include a sarcoid-type epithelioid granuloma in roughly half of the clinical cases. Lesions of Crohn's Disease can be transmural including deep ulceration, edema, and fibrosis, which can lead to obstruction and fistula formation as well as abscess formation. This contrasts with ulcerative colitis which usually yields much shallower lesions, although occasionally the complications of fibrosis, obstruction, fistula formation, and abscesses are seen in ulcerative colitis as well.

Treatment is similar for both diseases and includes steroids, sulphasalazine and its derivatives, and immuno-suppressive drugs such as cyclosporin A, mercaptopurine and azathioprine. More recently developed treatments, some still in clinical trials, involve systemic administration (by injection) of TNF blocking compounds such as TNF-antibodies or soluble TNF receptor.

IBD represents a genuine problem in public health because of the absence of etiologic treatment. Although many patients are managed successfully with conventional medical therapy, such as anti-inflammatory corticosteroid treatment, most will have recurrent activity of disease, and two-thirds will require surgery.

The cause of inflammatory bowel diseases is unknown. The pathogenesis of CD and UC probably involves interaction between genetic and environmental factors, such as bacterial agents, although no definite etiological agent has been identified so far. The main theory is that abnormal immune response, possibly driven by intestinal microflora, occurs in IBD. It is well established that T-cells play an important role in the pathogenesis. Activated T-cells can produce both anti-inflammatory and pro-inflammatory cytokines. With this knowledge in hand, IBD can be counteracted in a rational manner. Novel anti-inflammatory therapies, which make use of neutralizing monoclonal antibodies or anti-inflammatory cytokines, show the possibility to modulate the immune disregulations causative to IBD. A highly prominent and effective new therapy is systemic treatment with anti-TNF monoclonal antibodies as mentioned above. Single intravenous doses, ranging from 5 to 20 mg/kg, of the cA2 infliximab antibody resulted in a drastic clinical improvement in active Crohn's disease. The use of systemically administered recombinant IL-10 in a 7 day by day treatment regime using doses ranging from 0.5 to 25 µg/kg showed reduced Crohn's disease activity scores and increased remission. A number of very promising therapies, either tangling pro-inflammatory cytokines or the establishment of T-cell infiltrates, are currently emerging from experimental models. All these strategies however require systemic administration. The severe complications of IBD can be seriously debilitating, and eventually may lead to death.

In U.S. Pat. No. 5,368,854, assigned to Schering Corp., a method is disclosed for using IL-10 to treat inflammatory bowel diseases in mammals. In this method, the cytokine is administered to a mammal having IBD. The administration of IL-10 as described in this reference is parenteral, such as intravascular, preferably intravenous. Such a route of administration for a (human) patient suffering from IBD is, however, not without drawbacks. A much easier and more convenient way would be oral administration of a medicament comprising a cytokine such as IL-10 or a cytokine-antagonist which has a similar therapeutic activity. More importantly, localized release of the therapeutic agent allows for higher efficacy and less unwanted side effects due to systemic activities.

In WO 97/14806, assigned to Cambridge University Technical Services Ltd., a method is disclosed for delivering biologically active polypeptides and/or antigens by using non-invasive bacteria, such as Lactococcus, by intranasally administering the polypeptides to the body, especially at the mucosa.

However, treating an inflammatory bowel disease such as chronic colitis or Crohn's disease with an acid sensitive cytokine like IL-10, is a very delicate and difficult task to accomplish. Therefore, a system needs to be developed wherein the active compound (e.g., a cytokine or a soluble receptor) is delivered directly at the place where the compound is expected to exert its activity taking into account the acid sensitivity of many cytokines, particularly IL-10, since, after oral administration, the delivery vehicle needs to pass through the acidic environment of the stomach. Furthermore, various digestive enzymes degrade polypeptides as they pass through the stomach and the gut. Last, but not least, in situ administration of the agent may allow one to reach therapeutically effective concentrations difficult to achieve by most systemic routes of administration due to systemic toxicity or other limitations.

SUMMARY OF THE INVENTION

The invention generally relates to an administration strategy for delivering cytokines, preferably of acid sensitive anti-inflammatory agents, such as IL10 and/or a soluble TNF receptor, via the oral route to the intestinal mucosa. The invention preferably involves inoculation along with a suspension of live recombinant Lactococcus lactis cells engineered to produce the respective proteins. For example, mice having a chronic inflammation of the distal colon induced by administration with dextran sulfate sodium (DSS). The treatment, as scored by histological evaluation, clearly showed a regression of the inflammation and disease symptoms. The finding is highly unexpected since, in order to exert activity at the colon following oral administration, the delivery system had to pass the acidic environment of the stomach and the upper part of the small intestine.

DETAILED DESCRIPTION OF THE INVENTION

Figure 1:
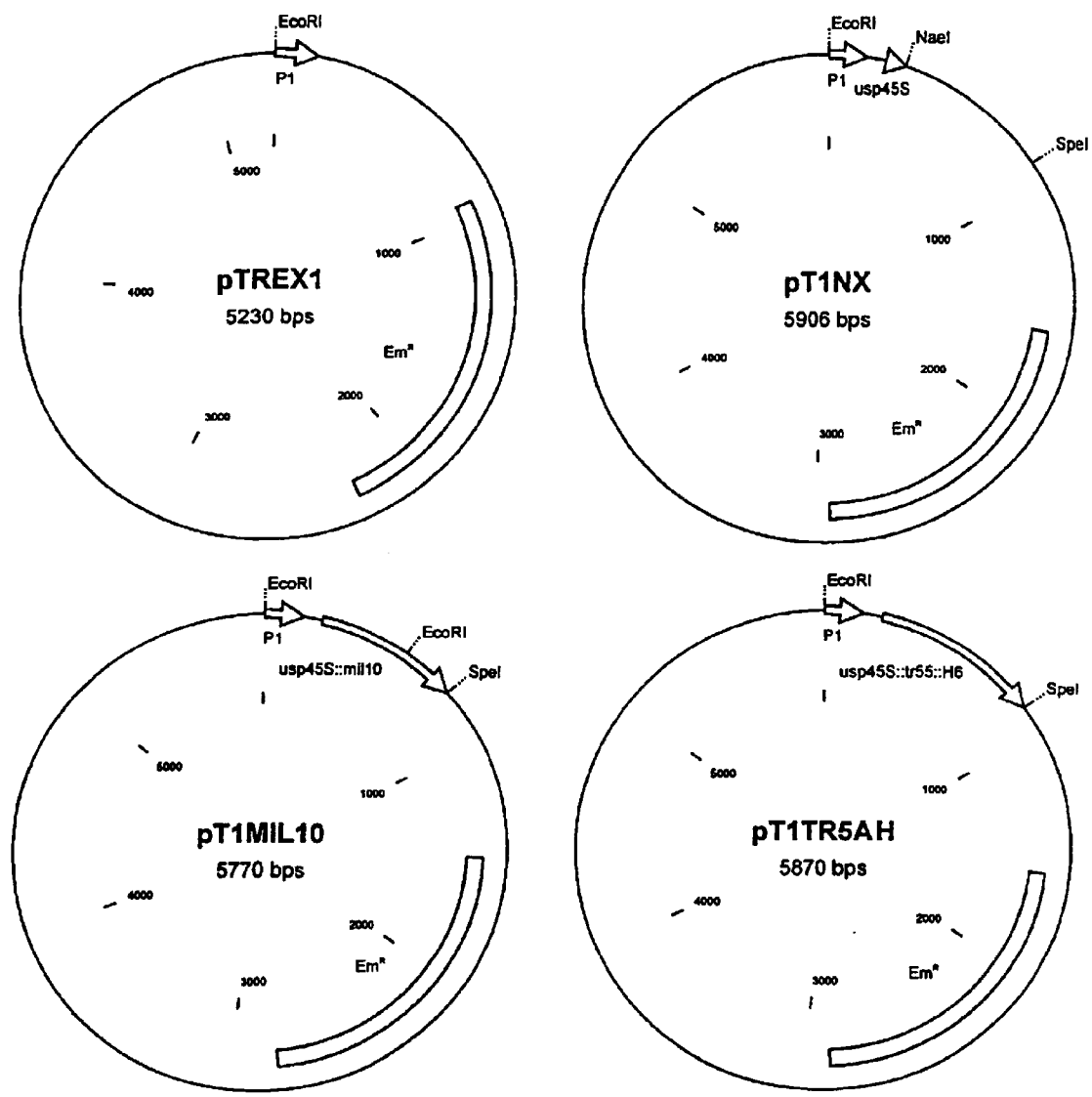
FIG. 1 depicts the schematic maps of the plasmids used. P1 is the lactococcal P1 promoter as in Waterfield et al, (1995), usp45S is a DNA fragment encoding the secretion signal peptide from the lactococcal Usp45 (van Asseldonck et al, 1990), mil 10 is a DNA fragment encoding the mature part of murine interleukin 10, tr55 is a DNA fragment encoding the soluble part of type 1 TNF receptor, H6 is a fragment encoding 6 histidine residues, Em is the erythromycin selection marker. The DNA sequences of pTREX1 (SEQ ID NO:5), pT1NX (SEQ ID NO:6), pT1MIL10 (SEQ ID NO:7), and pT1TR5AH (SEQ ID NO:8) are listed in the enclosed sequence listing and incorporated herein by reference.

In order to achieve the recovery of a patient suffering from an IBD, it is necessary to restore the damaged cells and the organ comprising the damaged cells, for instance the colon. The solution to the above described technical problem is achieved by providing the embodiments characterized below.

According to the invention, cytokine-producing Gram-positive bacterial strain or a cytokine antagonist producing Gram-positive bacterial strain is used for the preparation of a medicament to treat inflammatory bowel disease.

The cytokine or cytokine antagonist to be produced by the bacterial host strain is, for instance, IL-10, a soluble TNF receptor or a cytokine analogue such as the IL-12 derived p40 homodimer (an IL-12 antagonist), an Interferon-γ-antagonist, an IL-1 antagonist or a virus-coded cytokine analogue such as EBV BCRF1 (Baer et al., 1984), whereas the Gram-positive bacterial strain preferably is a Lactococcus species, and more preferably, a *Lactococcus lactis*.

Other Gram-positive bacterial strains to be used for the purpose of the current invention are *Bacillus subtilis, Streptococcus gordonii, Staphylococcus xylosus*, or a Lactobacillus species, such as *L. bulgaricus, L. salivarius, L. casei; L. helveticus, L. delbrueckii* or *L. plantarum*.

The inflammatory bowel diseases such as a chronic colitis, Crohn's disease and ulcerative colitis can be treated according to the invention with an appropriate dosage of the active cytokine compound, preferably IL-10 or soluble TNF receptor. The treatment unexpectedly restores the diseased colon to an apparently normal and healthy state.

IL-10 can be administered alone or in combination with at least one additional therapeutic agent. Examples of such additional therapeutic agents include corticosteroids, sulphasalazine, derivatives of sulphasalazine, immunosuppressive drugs such as cyclosporin A, mercaptopurine, azathioprine, and another cytokine. The co-administration can be sequential or simultaneous. Co-administration generally means that the multiple (two or more) therapeutics are present in the recipient during a specified time interval. Typically, if a second agent is administered within the half-life of the first agent, the two agents are considered co-administered.

The invention disclosed herein thus concerns a localized delivery of IL-10 through in situ synthesis by recombinant L lactis. As a result thereof, the inflammation is reduced by 50% in chronic colitis induced with DSS, and prevents the onset of colitis in IL-10-/- 129 Sv/Ev mice. So the method is equally efficient in comparison to powerful, well-established and accepted therapies relying on the systemic administration of anti-inflammatory proteins.

The vector, L. lactis, is a Gram positive food grade organism which is believed to be totally harmless. It is a non-colonizing micro-organism. Accurate dosage and timing during treatment, shown here to be of great importance, can thus easily be obtained.

The critical requirement for viability of the vector is shown in the current invention. This indicates the need for in situ synthesis of IL-10. The vector is indeed capable of achieving this by showing de novo synthesis of IL-10 in the colon.

An efficient novel concept for protein-based treatment in the intestinal tract is herein disclosed. The treatment can be given by the oral route, which is by far the most desirable for pharmacological formulations. It can exert effects up to the distal colon using a compound with intrinsic sensitivity for the route used. This method bypasses the need for systemic administration. It opens the possibility for the localized delivery of substances, which are unstable or difficult to produce in high quantities. Intrinsically, it is very cost effective. In comparison to systemic delivery, the method may provide for sustained and localized presence of IL-10 at concentrations higher than desirable or even achievable with systemic delivery, especially with regard to latent side effects.

Some terms used in the current description are, for sake of clarity, explained hereafter.

Generally, the term "symptoms" refers to any subjective evidence of disease or of a patient's condition. This includes evidence as perceived by the patient. Examples of symptoms of IBD include diarrhea, abdominal pain, fever, melena, hematochezia, and weight loss.

The-term "signs" refers generally to any objective evidence of a disease or condition, usually as perceived by an examining physician or features which would reveal themselves on a laboratory evaluation or other tests such as an ultrasonic study or a radiographic test. Some examples of signs of IBD include abdominal mass, glossitis, aphtous ulcer, anal fissure, perianal fistula, anemia, malabsorption, and iron deficiency. Occasionally, signs and symptoms overlap. For example, the patient complains of blood stools (a symptom), and a laboratory test of a stool sample is positive for blood (a sign).

The phrase "appropriate dosage" or "effective amount" means an amount or dosage sufficient to ameliorate a symptom or sign of an autoimmune condition or of an undesirable or inappropriate inflammatory or immune response. An effective amount for a particular patient may vary depending on factors such as the condition being treated, the overall health of the patient, the method, route and dose of administration and the severity of the side affects.

With "cytokine" is meant a polypeptide factor produced transiently by a range of cell types, acting usually locally, and activating the expression of specific genes by binding to cell surface receptors.

With "antagonist" is meant a compound that binds to but does not activate receptors, and hence inhibits the action of an agonist competitively.

"Agonists" are compounds that bind to and activate receptors (e.g., endogenous ligands such as hormones and neurotransmitters, chemically synthesized compounds, natural products like alkaloids).

The invention is further explained by the following methods used in the current invention.

Culture Media

GM17 is M17 (Difco, St. Louis, Mo., U.S.) supplemented with 0.5 w/v % of glucose. GM17E is GM17-supplemented with 5 μg/ml of erythromycin. BM9 contains per liter 6 g of $N_2HPO_4$, 3 g of $KH_2PO_4$, 1 g of $NH_4Cl$, 0.5 g of NaCl, 2 mmol of $MgSO_4$, 25 mmol of $NaHCO_3$, 25 mmol of $Na_2CO_3$, 0.1 mmol of $CaCl_2$, 5 g of glucose and 5 g of casitone (Difco). BM9E is BM9 supplemented with 5 μg/ml of erythromycin.

Recombinant DNA Techniques.

PCR amplification of DNA was performed with VENT polymerase and using conditions recommended by the manufacturer. DNA modifying enzymes and restriction endonucleases were used under standard conditions and in the buffers recommended by the manufacturers. General molecular cloning techniques and the electrophoresis of DNA and proteins were carried out essentially as described (Sambrook et al., 1990). *L. lactis* was transformed by electroporation of cells grown in the presence of glycine (Wells et al., 1993).

The plasmid pT1MIL10 (FIG. 1) was constructed by subcloning a PCR fragment, obtained with the primers (CAGTACAGCCGGGAAGACAAT (SEQ ID NO:1) and GCACTAGTTAGCTTTTCATTTTGAT (SEQ ID NO:2)) and performed on a cDNA clone containing mIL10 coding sequence. For the design of this strategy, we made use of the mIL10 cDNA sequence as given in EMBL acc. nr. M37897. By utilizing the above-mentioned primers, the mIL10 fragment could be subcloned as a blunt—SpeI fragment, after treatment with kinase and SpeI, in the NaeI-SpeI opened plasmid pT1NX (FIG. 1), which is a pTREX1 derivative (Wells and Schofield in: Lactic Acid Bacteria: current advances in metabolism, genetics and applications. F. Bozoglu & R. Bibek, Eds., Nato ASI Series H, Vol.98, p. 37. Springer-Verlag, 1996.)

The plasmid pT1TR5AH (FIG. 1) was constructed by subcloning a PCR fragment, obtained with the primers (CTGGTCCCTTCTCTTGGTGAC (SEQ ID NO:3) and CCACTAGTCTATTAATGATGATGATGAT-GATGCGCAGTACCTGAGTCCTGGGG (SEQ ID NO:4)) and performed on a cDNA clone containing sTNFr55 coding sequence. In designing this strategy, we made use of the TNFr55 cDNA sequence as given in EMBL acc. nr. L26349. By utilizing the above-mentioned primers, the sTNFr55 fragment was provided with a 6his tag at the 3' end and could be subcloned as a blunt—SpeI fragment, after treatment with kinase and SpeI in the NaeI-SpeI opened plasmid pT1NX.

Both plasmids code, downstream from the lactococcal P1 promoter, for fusion genes between the secretion leader from Usp45 (Van Asseldonk et al., *Gene*, 95, 155–160, 1990) and mIL10 and sTNFr 55, respectively. Upon secretion, the leader sequence is cleaved off.

Identification of Recombinant Proteins

Figure 2:
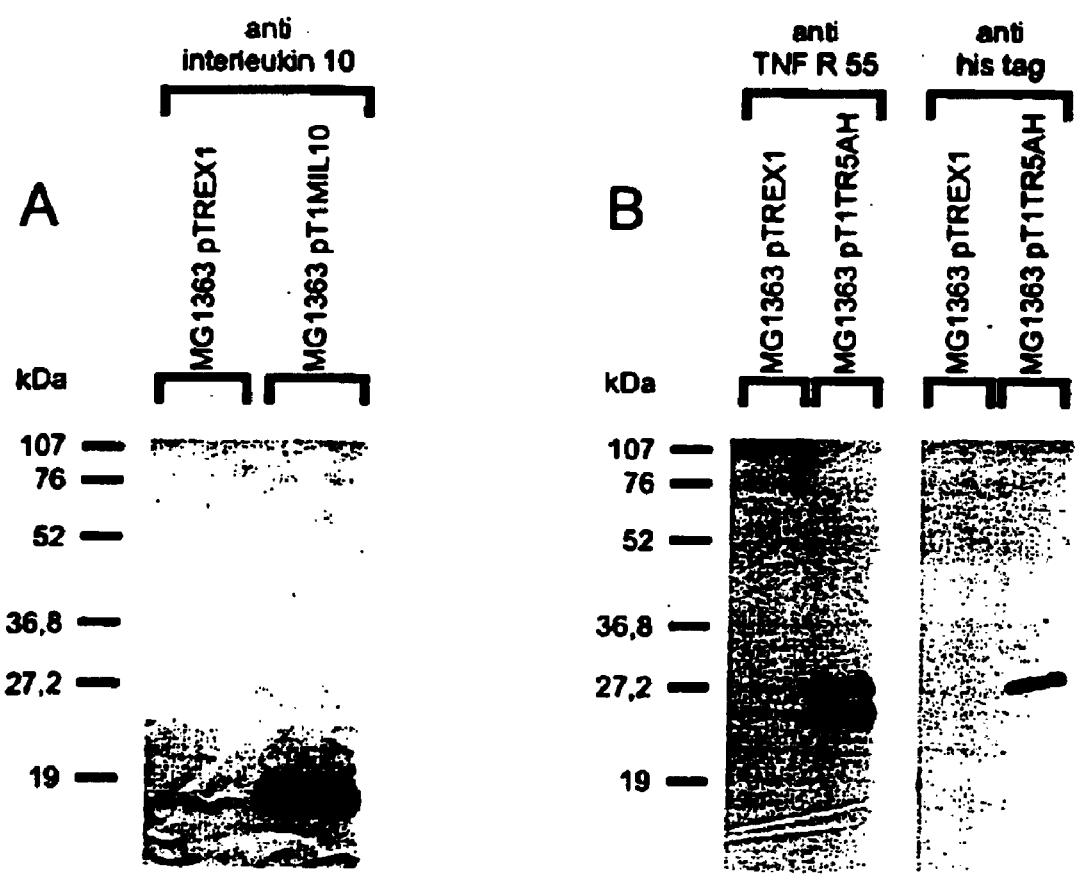
FIG. 2 illustrates the protein profile following SDS-PAGE of the culture supernatant of the indicated strains after immunoblot, revealed with anti-murine interleukin 10 (panel A) or anti-murine type 1 TNF receptor and anti-6 His (panel B) antisera.

Recombinant mIL10 and msTNFr 55 could be observed in the supernatant of cultures of MG1363(pT1MIL10) and MG1363(pT1TR5AH), respectively (FIG. 2). For this test, 5 ml aliquots of the cultures were extracted with 2 ml phenol and the proteins were subsequently prepared from the organic phase by precipitation with 10 ml of ethanol. A part of the precipitate, equivalent to 1 ml of culture supernatant, was subjected to SDS-15% PAGE and immunoblotting. Culture samples were taken at relevant times in the growth phase of the bacteria, as described below.

The culture supernatant of MG1363(pT1MIL10) contained, on average, 1 μg/ml of murine IL10. Murine IL-10activity of the supernatant was measured using a murine mast cell line MC/9 (Thompson-Snipes, L. et al., *J. Exp. Med.* 173, 507, 1991). Human IL-10 binds to murine IL-10R as was demonstrated by transfection experiments (Ho, A. S. Y et al., PNAS 90, 11267, 1993; Liu, Y. et al., *J. Immunol.* 152, 1821, 1994). 1 U/ml of IL-10 is defined as the amount of IL-10 that is able to inhibit 50% the level of IFN-gamma production of conA activated splenocytes (Fiorentino, D. F. et al., *J. Exp. Med.* 170,2081, 1989). The ED50 for this effect is typically 0.3-0.6 ng/ml. When measured along with a standard of known activity (Biosource International, CA) the MG1363(pT1MIL10) culture supernatant revealed an activity of approximately 8000 U/ml. Berg et al. (*J. Clin. Invest* 98, 1010-1020) report a specific activity of approximately $1.0 \times 10^7$ U/mg for recombinant mIL10. From these considerations, and taking into account the variations in the method used, we concluded that the recombinant mIL10, present in the MG1363(pT1MIL10) culture supernatant, displayed full biological activity. No IL10 activity could be detected in the supernatant of the control cultures, MG1363 or MG1363(pTREX1).

The culture supernatant of strain MG1363(pT1TR5AH) contained, on average,200 ng/ml msTNFr55. Loetscheret al. (1991) showed that complete inhibition of TNF cytotoxic activity by sTNFr 55 was only obtained from a molar ratio of 1000:1 of sTNFr 55 to TNF and higher. The soluble recombinant TNFr 55 which had been recovered from the culture supernatant of MG1363(pT1TR5AH) showed an equal inhibitory effect on TNF as had been reported for the indigenous product. This was demonstrated by mixing up and thus competing out a titration series of TNF with a titration series of recombinant sTNFr and measuring TNF activity in a cytotoxicity assay as described (Espevik, T and Nissen-Meyer, 1986).

Pretreatment of the Mice

For the induction of chronic colitis, mice were pretreated as described by Kojouharoff et al. *Clin Exp Immunol* 107, 353, 1997. Six to eight weeks old female Balb/c mice received four cycles of treatment with DSS. Each cycle consisted of 5% DSS in the drinking water for 7 days, followed by a 10-day interval during which they received normal drinking water. Four to six weeks after completion of the last DSS cycle, mice were treated with the *L. lactis* strains as indicated.

The invention is further explained by the use of the following illustrative examples.

EXAMPLES

Example 1
Treatment of the Mice With Live *L. lactis*

Storage of expression strains.

Freshly streaked cultures of the *L. lactis* expression strains were inoculated in 10 ml of GM17 or GM17E depending on the absence or presence of an expression plasmid and grown overnight at 30° C. The overnight cultures were diluted 1/100 in fresh GM17 or GM17E and pregrown for 3 hours at 30° C. The cells were harvested by centrifugation and resuspended in BGM9 or BGM9E, depending on the presence of plasmids. These cultures were grown for 5 hours at 30° C. The protein profile of these cultures was analyzed by performing Western immunoblotting on an equivalent of 1 ml of culture supernatant using either antiserum directed towards sTNFr 55 or IL10 respectively. The protein profile of sTNFr 55 and IL10 is shown in the appropriate lanes (FIG. 2). 5 ml of the original GM17 or GM17E overnight cultures were supplemented with 5 ml of glycerol and stored at −20° C. These stocks were used as starter material for several experiments. Protein analysis throughout a series of individual experiments showed that a high degree of reproducibility in the production of the recombinant proteins could be obtained by this procedure.

Weeks 1 and 2

Stock solutions of *L. lactis* strains were diluted 1/200 in 10 ml GM17 or GM17E and grown overnight at 30° C. The cells were harvested by centrifugation and resuspended in 1 ml BM9 or BM9E. Control, healthy mice and mice with induced colitis were inoculated on a daily basis with 100 µl aliquots of these cell suspensions.

Weeks 3 and 4

Stock solutions of *L. lactis* strains were diluted 1/200 in 10 nd GM17 or GM17E and grown overnight at 30° C. These cultures were diluted 1/25 in 10 ml of BM9 or BM9E and grown for 3 hours at 30° C. Aliquots of 200 µl were intragastrically (peroral) administered into mice on a daily basis.

Example 2
Determination of Histological Score

Histological score was determined essentially as described by Kojouharoff et al. I107, 353, 1997.

Mice were euthanized by cervical dislocation. The colon was removed and washed with PBS. The distal third of the colon was cut longitudinally, laid on filter paper and fixed with 10% formalin in PBS overnight. Sections of the parafin-embedded material were made longitudinally. Three 3-µm sections were cut at an intermediate distance of 200 µm. The sections were stained with haematoxylin-eosin. Histological analysis was performed in blind fashion. Mice were scored individually, and each score represented the mean of three sections.

Histology was scored as follows:

Infiltration: 0, no infiltrate; 1, infiltrate around crypt bases; 2, infiltrate reaching to *L. muscularis* mucosae; 3, extensive infiltration reaching the L. muscularis mucosae and thickening of the mucosa with abundant oedema; 4, infiltration of the L. submucosa.

Epithelial damage: 0, normal morphology; 1, loss of goblet cells; 2, loss of goblet cells in large areas; 3, loss of crypts; 4, loss of crypts in large areas and/or foci of polyploid regeneration.

Figure 3:
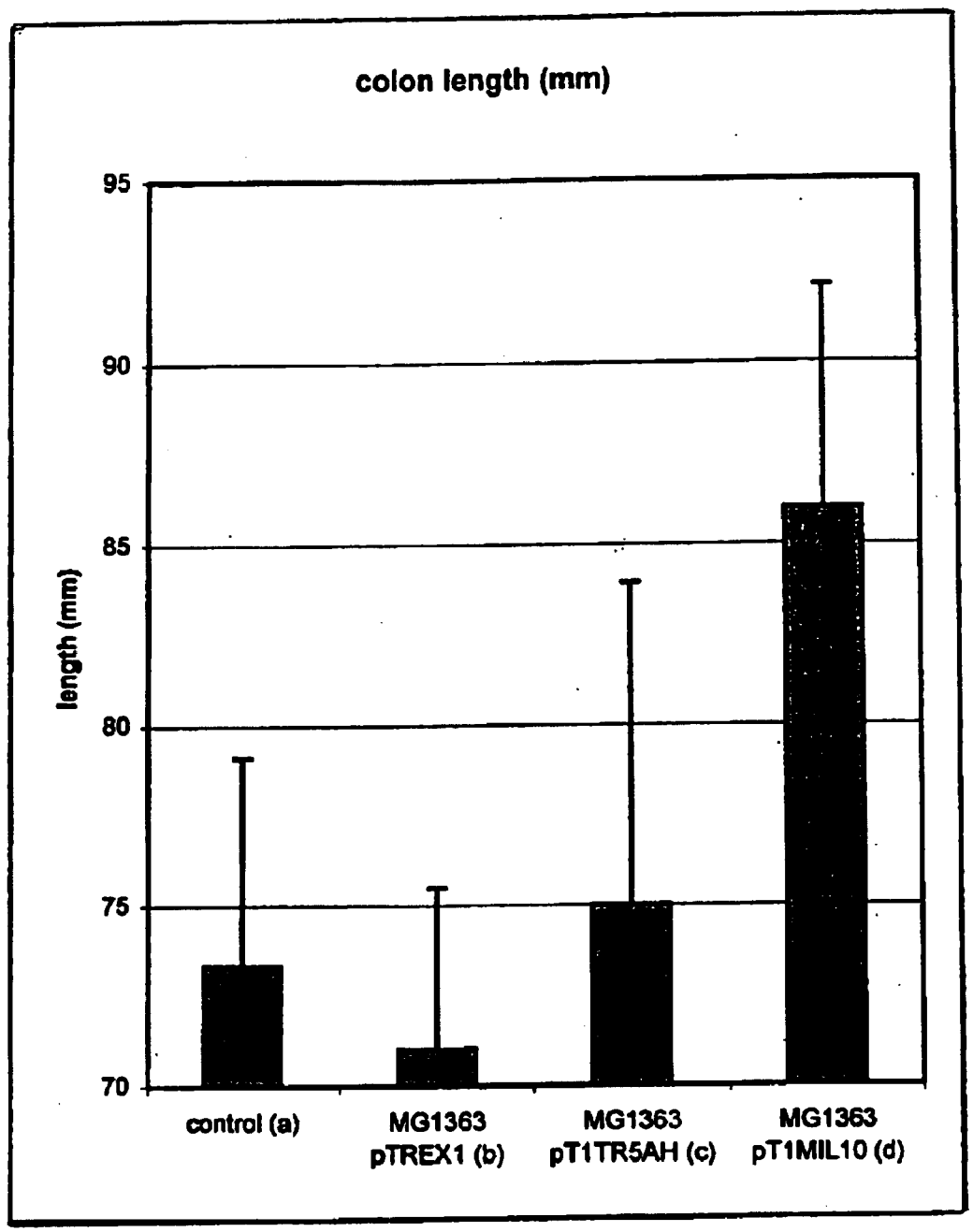
FIG. 3 is a bar graph depicting the average of colon length of groups of mice in which: a) chronic colitis had been induced with DSS, b) chronic colitis had been induced with DSS and to which subsequently L. lactis strain MG1363 (pTREX1) was orally administered, c) chronic colitis had been induced with DSS and to which subsequently L. lactis strain MG1363(pT1TR5AH) was orally administered and d) chronic colitis had been induced with DSS and to which subsequently L. lactis strain MG1363(pT1MIL10)was orally administered.

Colonic length was measured immediately after dissection and placement on a paper towel. The pathology of chronic colitis is, amongst other parameters, characterized by a decrease in length of the colon and by epithelial damage and infiltration of lymphocytes to a more or less substantial extent. FIG. 3 clearly shows an increase in colon length after the treatment of the inflamed mice with MG1363 (pT1MIL10) and, although to a lesser extent, after the treatment of the mice with MG1363(pT1TR5AH).

Figure 4:
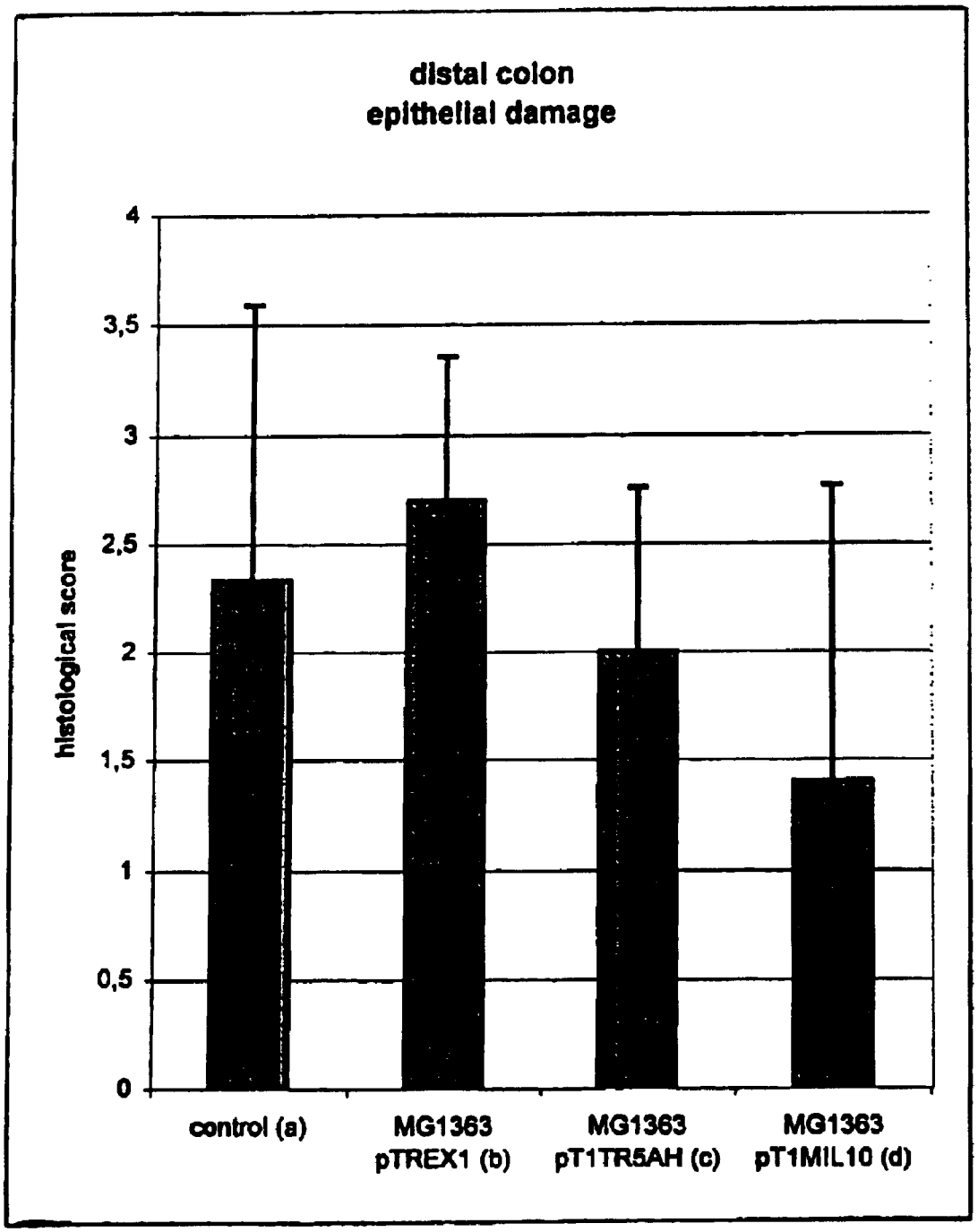
FIG. 4 is a bar graph depicting the average of epithelial damage score in the distal colon of groups of mice in which: a) chronic colitis had been induced with DSS, b). chronic colitis had been induced with DSS and to which subsequently L. lactis strain MG1363(pTREX1) was orally administered, c) chronic colitis had been induced with DSS and to which subsequently L. lactis strain MG1363 (pT1TR5AH) was orally administered and d) chronic colitis had been induced with DSS and to which subsequently L. lactis strain MG1363(pT1MIL10) was orally administered.
Figure 5:
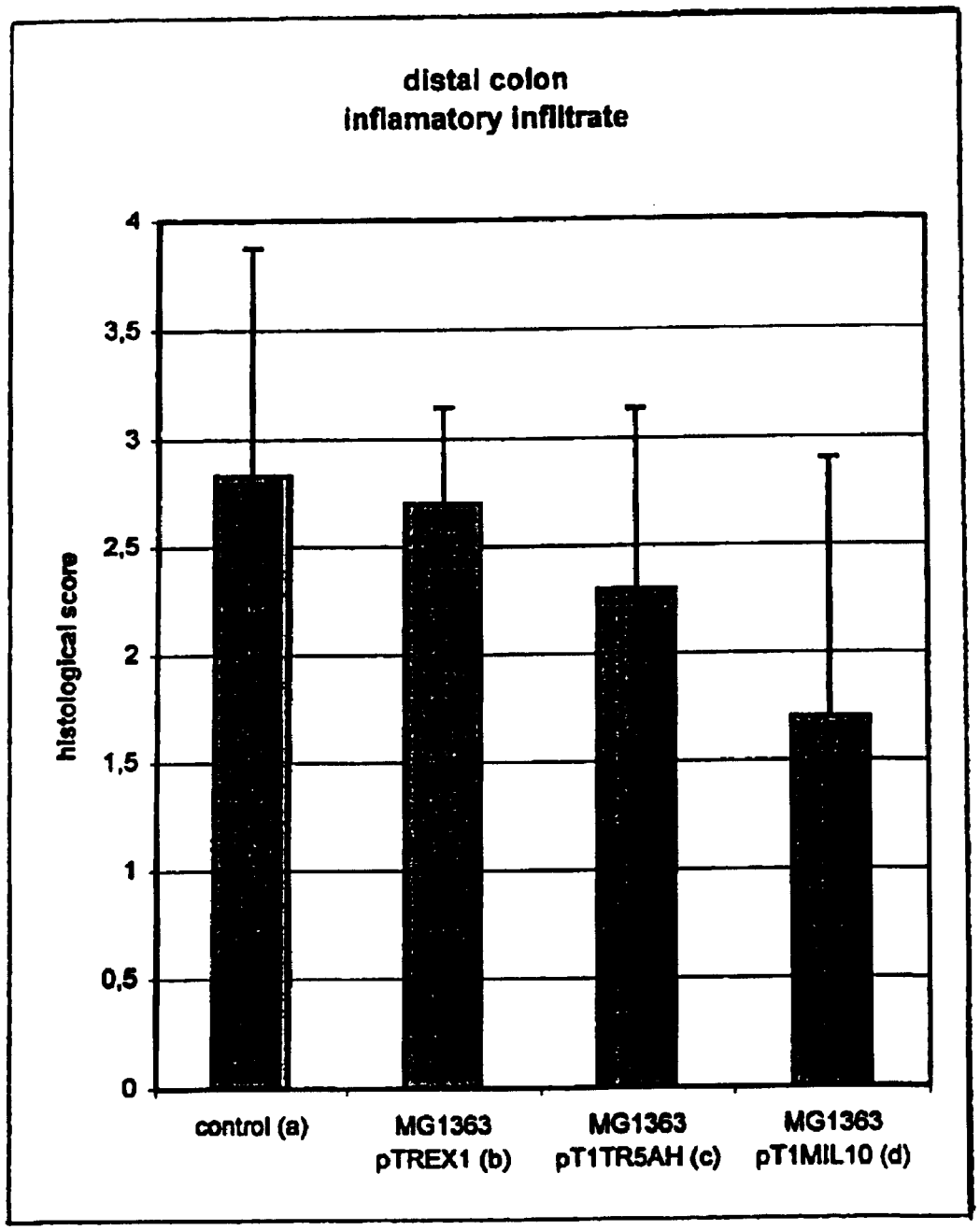
FIG. 5 is a bar graph depicting the average of inflammatory infiltrate score in the distal colon of groups of mice in which: a) chronic colitis had been induced with DSS, b) chronic colitis had been induced with DSS and to which subsequently L. lactis strain MG1363(pTREX1) was orally administered, c) chronic colitis had been induced with DSS and to which subsequently L. lactis strain MG1363 (pT1TR5AH) was orally administered and d) chronic colitis had been induced with DSS and to which subsequently L. lactis strain MG1363(pT1MIL10) was orally administered.
Figure 6:
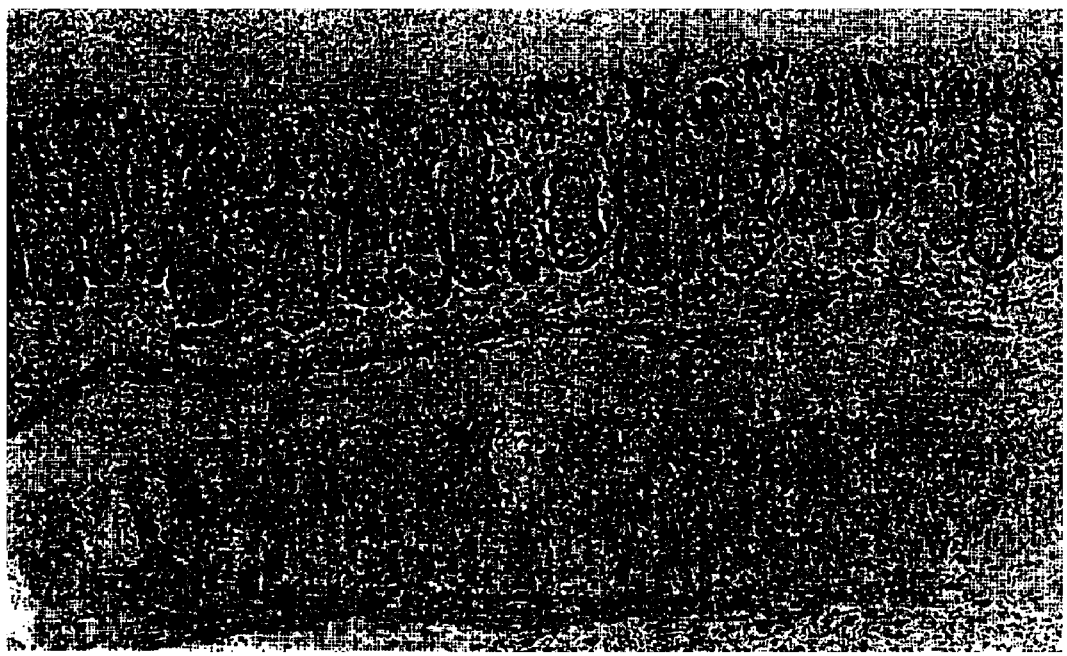
FIG. 6 shows representative sections of mice distal colon stained with haematoxylin and eosin. Specifically, the picture shown illustrates normal tissue in untreated animals.
Figure 7:
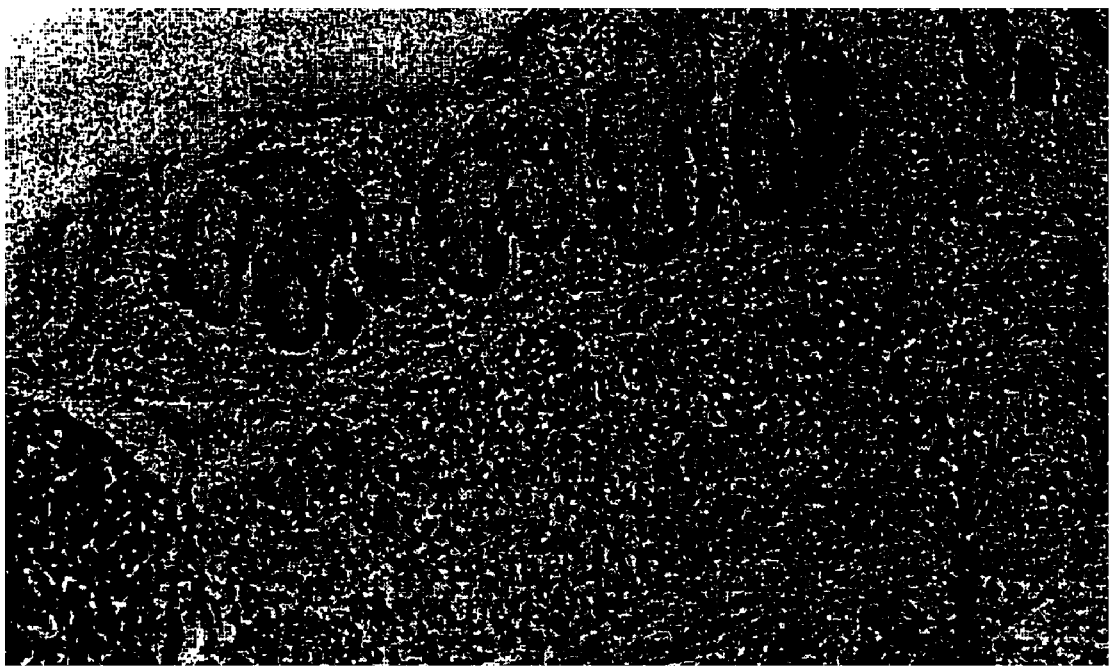
FIG. 7 shows representative sections of mice distal colon stained with haematoxylin and eosin. Specifically, the picture shown illustrates animals pretreated with DSS to acquire chronic colitis.
Figure 8:
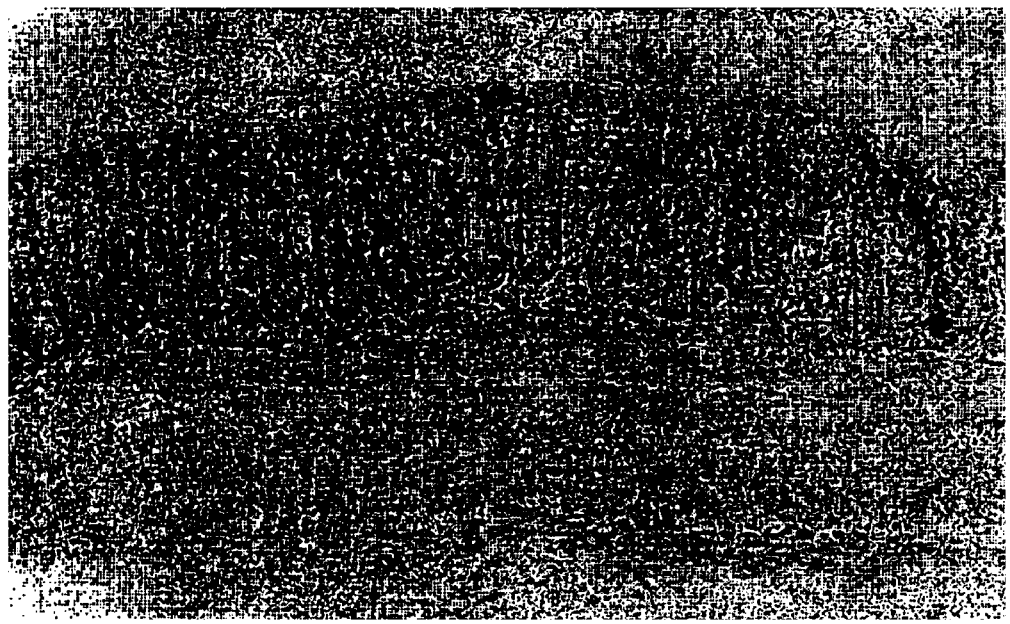
FIG. 8 shows representative sections of mice distal colon stained with haematoxylin and eosin. Specifically, the picture shown illustrates animals pretreated with DSS to acquire chronic colitis to which L. lactis strain MG1363 (pT1MIL10) was subsequently orally administered.
Figure 9:
FIG. 9 shows representative sections of mice distal colon stained with haematoxylin and eosin. Specifically, the picture shown illustrates animals pretreated with DSS to acquire chronic colitis to which L. lactis strain MG1363 (pTREX1) was subsequently orally administered.

FIGS. 4 and 5 show the onset of recovery from chronic colitis, in which mice treated with MG1363(pT1MIL10) appear to improve more extensively than those mice which had been treated with MG1363(pT1TR5AH).

FIG. 4 shows the histological score of epithelial damage whereas FIG. 5 shows inflammatory infiltrate, both determined as described previously.

FIGS. 6–9 shows the histology of normal tissue, compared to inflamed and treated tissue.

In the normal histology, one can observe a continuous array of crypts of equal length. In the crypts, numerous goblet cells can be observed. A low number of lymphocytes is present in the mucosa. No lymphocytes are present in the submucosa. In the inflamed tissue, one can see the disappearance of the organized crypt structures, ranging from differences in length to complete absence of structure. Also, in the relicts of the crypts no goblet cells are present. One can observe a large increase of the thickness of the mucosa due to a massive infiltration of lymphocytes. The lymphocytes tend to form ulcerations. In severe cases, infiltration of lymphocytes can also be observed in the submucosa. The epithelium, however, remains intact. The negative control of treatment with MG1363(pTREX1) shows a pathology reminescent of that of heavily inflamed tissue. Mice treated with MG1363 (pT1MIL10) show an almost complete restitution of the normal histology, revealing only slight remainders of infiltrating lymphocytes in the mucosa Mice treated with MG1363(pT1TR5AH) show an intermediate degree in pathology.

Figure 10:
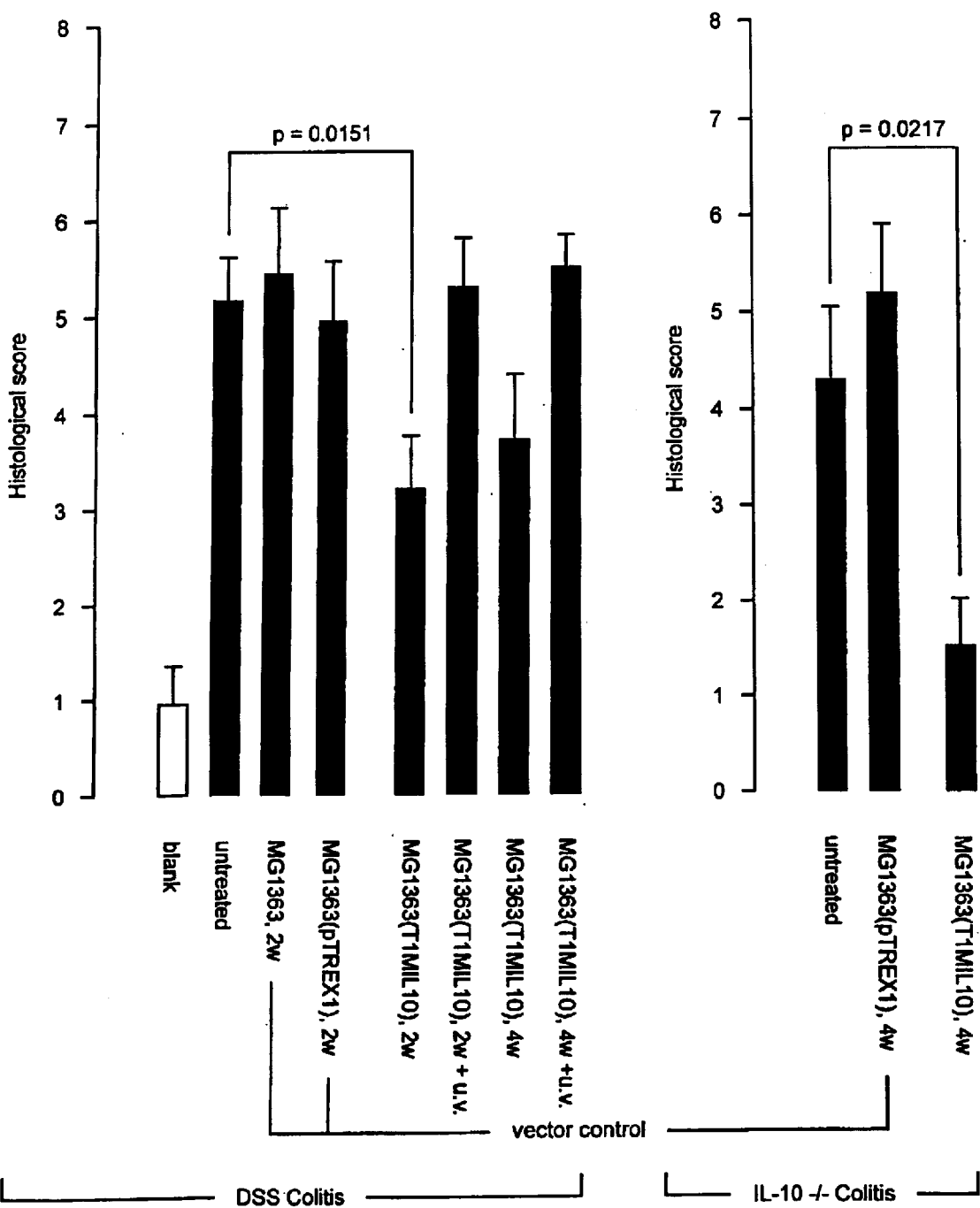
FIG. 10 is a graph illustrating statistical evaluation of the histology. The, colon sections were randomly numbered and interpreted blind. Scores from individual mice were subsequently decoded and the regrouped numbers were analyzed statistically. The DSS colitis panel shows histological sum scores for the distal colon of blank mice and of mice induced with DSS to acquire chronic colitis, either untreated or treated with L. lactis cultures. The score is a sum of scores for epithelial damage and lymphoid infiltrate, both ranging between 0 and 4. Groups of mice (n=10) were alternatively treated with MG1363, MG1363(pTREX1) or MG1363 (pT1MIL10) (=IL-10) for two (=2w) or four (=4w) weeks. Some of the cultures were irradiated with uv (=+uv) prior to inoculation, which reduced cell viability over $10^6$ times. The IL-10-/- colitis panel shows histological sum scores of groups (n=5) of 7 week old untreated, TREX treated and IL-10 treated female 129 Sv/Ev IL-10-/- mice. The histological score is a sum of the degree of inflammation in the proximal, middle and distal colon, all ranging between 0 and 4. Error bars represent s.e.m.

FIG. 10 shows the statistic evaluation of histological scores obtained from individual mice following treatment with the indicated *L. lactis* strains (group size=10). The score was recorded after blind interpretation of slides from the distal colon as described (Kojouharoff et al., 1997). Each mouse was interpreted according to 3 longitudinal slides, equally spaced over the circumference of the colon. Both lymphoid infiltrate and epithelial damage were rated from 0 to 4 points and values for both parameters were summed for every mouse. Normal blank mice showed a histological score of 1 point. The mice induced for colitis are slightly over 5 points. All of the control groups for *L. lactis* treatment fluctuate around this number, with possibly a slightly higher tendency in some groups. The mice treated for 14 days with mIL-10 producing *L. lactis*, followed by 14 days of recovery however show an average of approximately 3 points. This is a decrease of nearly 50% in the pathology when measured against the difference between untreated and blank control groups. The reduction is significant ($p=0.0151$).

Example 3

Figure 11:
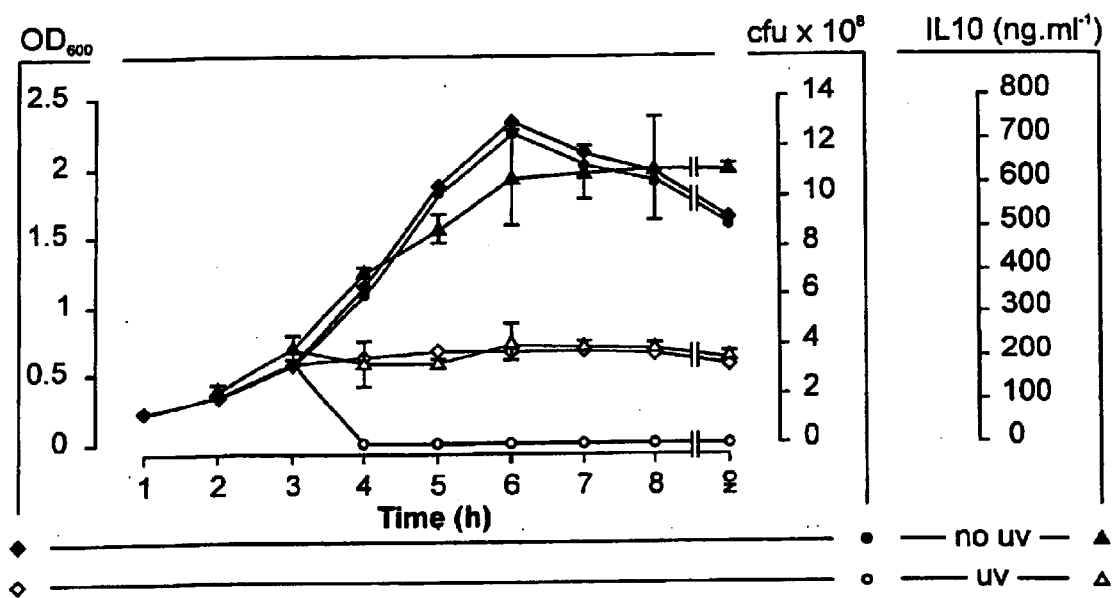
FIG. 11 is a graph that shows the representation of bacterial viability after irradiation as measured at $OD_{600}$.

Due to the culture conditions used, a minor amount (40 ng) of mIL-10 is present in the supernatant of the inoculation suspension. To investigate whether this IL-10 brings about the observed reduction in the histological score we included treatment with UV killed IL-10 producer strains. These cultures were UV irradiated immediately prior to the inoculation. FIG. 11 shows that irradiation reduced the bacterial viability to less than 1 in $10^6$ cfu so that no further accumulation of L-10 was observed. This was not associated with cell lysis since no drop in $OD_{600}$ was observed and no IL-10 precursor could be detected in the culture supernatant. The irradiation does not affect IL-10 bioactivity. Diseased mice treated for 2 or 4 weeks with the UV dispatched cultures show no difference in colon histology when compared to any of the control groups positive for enterocolitis. The fate of the residual IL-10 in the inoculation medium is most likely denaturation and breakdown in the stomach and duodenum. The acidity of the stomach, prior at pH 1.5, rises to pH6 immediately after inoculation. After 5 minutes a pH of 4 is reached, which further drops from 3.5 to 2.5 in the interval between 30 and 60 minutes after inoculation. IL-10 detected in the stomach 5 minutes after inoculation rapidly decreases in concentration and was only found in trace amounts in the duodenum at 30 minutes after inoculation. At later time-points, no IL-10 was detected here nor in the jejunum or ileum.

Example 4

Seven serial inoculations of $3.4 \times 10^9$ cfu of MG1363 (pT1MIL10) were given to 129 Sv/Ev IL-10-/- mice, thereby respecting 1 hour intervals. The intestine was prepared out 30 minutes after the last inoculation and divided in the morphologic compartments. Immediately the tissues were homogenized in PBS with 1% BSA and 0.05% $NaN_3$. Cfu of MG1363(pT1MIL10) were determined as $7 \times 10^6$ in the stomach, $2.6 \times 10^8$ in the duodenum, $2.8 \times 10^7$ in the jejunum, $4 \times 10^8$ in the ileum, $8.4 \times 10^8$ in the caecum and $7 \times 10^8$ in the colon. We have detected 70 ng of soluble IL-10 in the colon homogenate. None of the upstream compartments showed any IL-10 content. From this it is concluded that recombinant L. lactis can actively produce IL-10 in the colon.

Example 5
Prevention of Enterocolitis in IL10-/- Mice

The capacity of the approach described above was tested to prevent the onset of colitis in 129 Sv/Ev IL10-/- mice. These mice spontaneously developed a generalized enterocolitis in the frame between three and eight weeks of age (Kuhn et al., Cell, 1993; 75:263–274). Inflammatory changes first appear in the cecum, ascending and transverse colon of 3-wk-old mutants. Progressive disease in aging IL10-/- mice was characterized by an increased number of multifocal inflammatory cell infiltrates composed of mononuclear cells and neutrophils accompanied by moderate epithelial hyperplasia and slight mucin depletion from goblet cells. Small epithelial erosions and crypt abscesses were occasionally present and inflammation rarely involved the submucosa. IL10-/- mice used in our studies showed a less severe inflammation as described due to "clean" rather than "conventional" conditions of our animal facility.

When these mice are treated from week 3 on, for 6 to 8 weeks with either anti IFN-γ or anti-IL-12 colitis can be prevented (Rennick et al., J-Leukoc-Biol., 1997 April; 61(4): 389–396). We treated 3 weeks old mice by daily intra-gastric inoculation with IL-10 producing L. lactis. The mice were treated for 4 weeks with either mid-log or end-log cultures whilst an untreated group was kept under identical conditions. FIG. 10 shows histological scores obtained as described (Berg et al., J-Clin-Invest; 1996, Aug. 15;98(4): 1010–1020), with the exception that we did not examine the caecum. The nontreated mice show a mean histological score of approximately 4.5 points. This fits well with reported data, provided one takes into account the contribution of the caecal scores in these values and the slight age difference. The group of mice treated with MG1363 (pT1MIL10) shows a mean histological score of 1.5 points which is only slightly over values reported for 3 week old mice (Berg et al., J-Clin-Invest; 1996, Aug 15;98(4): 1010–1020). As it is the sum of 3 values ranging from 0 to 4 points, this is considered as a very low score. From these data it is clear that the development of colitis can be prevented by this treatment.

References

Wells J. M., & Schofield, K. M. Cloning and expression vectors for lactococci From: Lactic Acid Bacteria (eds Bozoglu B., and Ray, B.) NATO ASI Series H 98: 37–63 Springer-Verlag, Berlin, Heidelberg (1996).

Kojouharoff, G., Hans, W., Obermeler, F., Mannel, D. N., Andus, T., Scholmerich, J., Gross, V. & Falk; W. Neutralization of tumour necrosis factor (TNF) but not of IL-1 reduces inflammation in chronic dextran sulphate sodium-induced colitis in mice. Clin. Exp. Immunol. 107, 353–358, 1997.

Van Asseldonk, M, Rutten, G., Oteman, M., Siezen, R. J., de Vos, W. M. and Simons, G. Cloning of usp45, a gene encoding a secreted protein from Lactococcus lactis subsp. lactis MG1363. Gene, 95, 155–160 (1990).

Sambrook, J., Fritsch, E. F., and Maniatis T. Molecular cloning-a laboratory manual. Cold Spring Harbor Laboratory, New York (1990).

Wells, J. M., Wilson, P. W., and Le Page, R. W. F. Improved cloning vectors and transformation procedure for Lactococcus lactis. J. AppL Bacteriol. 74, 629–636 (1993).

Schlaak, J. F., Schmitt, E., Huls, C., Meyer zum Buschenfelde, K. H. & Fleischer, B. A sensitive and specific bioassay for the detection of human interleukin-10. J. Immunol. Methods 168, 49–54, 1994.

Thompson-Snipes, L., Dhar, V., Bond, M. W., Mosmann, T. R., Moore, K. W. & Rennick, D M Interleukin 10: a novel stimulatory factor for mast cells and their progenitors. J. Exp. Med. 173, 507–10, 1991.

Ho, A., S., Y., Liu, Y., Khan, T., A., Hsu, D., H., Bazan, J., F. & Moore, K., W. A receptor for interleukin 10 is related to interferon receptors. PNAS 90(23): 11267–11271 (1993)

Liu, Y., Wei, S., H., Y., Ho, A., S., Y., De Waal-Malefyt, R. & Moore, K., W. Expression cloning and characterization of a human IL-10 receptor. Journal of Immunology 152(4): 1821–1829 (1994)

Fiorentino, D. F., Bond, M. W. & Mosmann, T. R. Two types of mouse T helper cell. IV. Th2 clones secrete a factor that inhibits cytokine production by Th1 clones. J-Exp-Med. 170, 2081–95, 1989.

Waterfield, N. R. et al., The isolation of lactococcal promoters and their use in investigating bacterial luciferase synthesis in lactococcus lactis. Gene, 165, 9–15 (1995).

Baer, R. et al., DNA sequence and expression of the B95-8 Epstein-Barr virus genome. Nature, 130, 207–211 (1984).

What is claimed is:

1. A method of treating inflammatory bowel disease in a mammal, said method comprising:

administering a medicament to a mammal with inflammatory bowel disease comprising an amount of a cytokine- or cytokine antagonist-producing genetically modified non-invasive Gram-positive bacterial strain, wherein the administration of said medicament results in reduction of intestinal mucosal inflammation by at least 50%, wherein said cytokine or cytokine-antagonist is selected from the group consisting of IL-10, a soluble TNF receptor, a TNF antagonist, an IL-12 derived homodimer, and EBV BCRF1.

2. The method according to claim 1 wherein the non-invasive Gram-positive bacterial strain is a Lactococcus species.

3. The method according to claim 2 wherein the Lactococcus species is *Lactococcus lactis*.

4. The method according to claim 1 wherein the bowel disease is Crohn's Disease.

5. The method according to claim 1 wherein the medicament is administered in combination with at least one additional therapeutic agent.

6. The method according to claim 5 wherein the at least one therapeutic agent includes at least one immunosuppressive drug.

7. The method according to claim 5 wherein the co-administration of at least one additional therapeutic agent is sequential or simultaneous.

8. The method according to claim 1 wherein the medicament is delivered through in situ synthesis by recombinant *Lactococcus lactis*.

9. The method according to claim 1, wherein the cytokine is IL-10 and the non-invasive Gram-positive bacterial strain is a Lactococcus species.

10. The method according to claim 9 wherein the Lactococcus species is *Lactococcus lactis*.

11. The method according to claim 9, wherein the bowel disease is Crohn's Disease.

12. The method according to claim 9 wherein the medicament is administered in combination with at least one additional therapeutic agent.

13. The method according to claim 12 wherein the at least one therapeutic agent includes at least one immunosuppressive drug.

14. The method according to claim 12 wherein the co-administration of at least one additional therapeutic agent is sequential or simultaneous.

* * * * *

UNITED STATES PATENT AND TRADEMARK OFFICE
CERTIFICATE OF CORRECTION

PATENT NO. : 6,746,671 B2
APPLICATION NO. : 09/838718
DATED : June 8, 2004
INVENTOR(S) : Lothar Steidler, Erik R. Remaut and Walter Fiers Page 1 of 1

It is certified that error appears in the above-identified patent and that said Letters Patent is hereby corrected as shown below:

On the title page:
In "Other Publications,"
2nd col., 10th line:                           change "Croh's," to --Crohn's,--

In the specification:
| | | |
|---|---|---|
| COLUMN 2, | LINE 5, | change "correspond-to" to --correspond to-- |
| COLUMN 2, | LINE 10, | change "younger-age." to --younger age.-- |
| COLUMN 2, | LINE 37, | change "sharplydemarcated" to --sharply demarcated-- |
| COLUMN 4, | LINE 23, | change "EM" to --EM$^r$-- |
| COLUMN 4, | LINE 47, | change "b)." to --b)-- |
| COLUMN 5, | LINE 16, | change "The," to --The-- |
| COLUMN 5, | LINE 63, | change "*casei;*" to --*caseï,*-- |
| COLUMN 6, | LINE 17, | change "L lactis." to --*L. lactis.*-- |
| COLUMN 7, | LINE 22, | change "GM17-supplemented" to --GM17 supplemented-- |
| COLUMN 7, | LINE 24, | change "N$_2$HPO$_4$," to --Na$_2$HPO$_4$,-- |
| COLUMN 8, | LINE 21, | change "IL-10activity" to --IL-10 activity-- |
| COLUMN 9, | LINE 36, | change "nd" to --ml-- |
| COLUMN 12, | LINE 17, | change "Obermeler," to --Obermeier,-- |

In the claims:
| | | | |
|---|---|---|---|
| CLAIM 2, | COLUMN 35, | LINE 16, | change "Lactococcus" to --*Lactococcus*-- |
| CLAIM 3, | COLUMN 35, | LINES 18-19, | change "Lactococcus" to --*Lactococcus*-- |
| CLAIM 9, | COLUMN 36, | LINE 10, | change "Lactococcus" to --*Lactococcus*-- |
| CLAIM 10, | COLUMN 36, | LINES 11-12, | change "Lactococcus" to --*Lactococcus*-- |

Signed and Sealed this

Fifteenth Day of August, 2006

JON W. DUDAS
*Director of the United States Patent and Trademark Office*

SEQUENCE LISTING

<160> NUMBER OF SEQ ID NOS: 8

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: primer used
      for obtaining the plasmid pT1MIL10

<400> SEQUENCE: 1
cagtacagcc gggaagacaa t                                              21

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: primer used
      for obtaining the plasmid pT1MIL10

<400> SEQUENCE: 2
gcactagtta gcttttcatt ttgat                                          25

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: primer used
      for obtaining the plasmid pT1TR5AH

<400> SEQUENCE: 3
ctggtccctt ctcttggtga c                                              21

<210> SEQ ID NO 4
<211> LENGTH: 53
<212> TYPE: DNA
<213> ORGANISM: Artificial Sequence
<220> FEATURE:
<223> OTHER INFORMATION: Description of Artificial Sequence: primer used
      for obtaining the plasmid pT1TR5AH

<400> SEQUENCE: 4
ccactagtct attaatgatg atgatgatga tgcgcagtac ctgagtcctg ggg           53

<210> SEQ ID NO 5
<211> LENGTH: 5230
<212> TYPE: DNA
<213> ORGANISM: Artificial Sequence
<220> FEATURE:
<223> OTHER INFORMATION: Description of Artificial Sequence: plasmid
      pTREX1

<400> SEQUENCE: 5
gaattcgatt aagtcatctt acctctttta ttagtttttt cttataatct aatgataaca     60
tttttataat taatctataa accatatccc tctttggaat caaaatttat tatctactcc    120
tttgtagata tgttataata caagtatcag atctgggaga ccacaacggt ttcccactag    180
aaataatttt gtttaacttt agaaaggaga tatacgcatg caggatatct ctagaatgga    240
tccggctgct aacaaagccc gaaaggaagc tgagttggct gctgccaccg ctgagcaata    300
actagcataa ccccttgggg cctctaaacg ggtcttgagg ggttttttgc tgaaaggagg    360

-continued

```
aactatatcc ggatgacctg caggcaagct ctagaatcga tacgattttg aagtggcaac    420
agataaaaaa aagcagttta aaattgttgc tgaactttta aaacaagcaa atacaatcat    480
tgtcgcaaca gatagcgaca gagaaggcga aacattgcc tggtcgatca ttcataaagc     540
aaatgccttt tctaaagata aaacgtataa aagactatgg atcaatagtt tagaaaaaga   600
tgtgatccgt agcggttttc aaaatttgca accaggaatg aattactatc ccttttatca    660
agaagcgcaa aagaaaaacg aaatgataca ccaatcagtg caaaaaaaga tataatggga    720
gataagacgg ttcgtgttcg tgctgacttg caccatatca taaaaatcga aacagcaaag   780
aatggcggaa acgtaaaaga agttatggaa ataagactta gaagcaaact taagagtgtg    840
ttgatagtgc agtatcttaa aatttttgtat aataggaatt gaagttaaat tagatgctaa   900
aaatttgtaa ttaagaagga gtgattacat gaacaaaaat ataaaatatt ctcaaaactt    960
tttaacgagt gaaaaagtac tcaaccaaat aataaaacaa ttgaatttaa agaaaccga   1020 taccgtttac gaaattggaa caggtaaagg gcatttaacg acgaaactgg ctaaaataag   1080
taaacaggta acgtctattg aattagacag tcatctattc aacttatcgt cagaaaaatt   1140
aaaactgaat actcgtgtca ctttaattca ccaagatatt ctacagtttc aattccctaa   1200
caaacagagg tataaaattg ttgggagtat tccttaccat ttaagcacac aaattattaa   1260
aaaagtggtt tttgaaagcc atgcgtctga catctatctg attgttgaag aaggattcta   1320
caagcgtacc ttggatattc accgaacact agggttgctc ttgcacactc aagtctcgat   1380
tcagcaattg cttaagctgc cagcggaatg ctttcatcct aaaccaaaag taaacagtgt   1440
cttaataaaa cttacccgcc ataccacaga tgttccagat aaatattgga agctatatac   1500
gtactttgtt tcaaatgggt caatcgaga atatcgtcaa ctgtttacta aaaatcagtt   1560
tcatcaagca atgaaacacg ccaaagtaaa caatttaagt accgttactt atgagcaagt   1620
attgtctatt tttaatagtt atctattatt taacgggagg aaataattct atgagtcgct   1680
tttgtaaatt tggaaagtta cacgttacta aagggaatgt agataaatta ttaggtatac   1740
tactgacagc ttccaaggag ctaaagaggt ccctagcgct cttatcatgg ggaagctcgg   1800
atcatatgca agacaaaata aactcgcaac agcacttgga gaaatgggac gaatcgagaa   1860
aaccctcttt acgctggatt acatatctaa taaagccgta aggagacggg ttcaaaaagg   1920
tttaaataaa ggagaagcaa tcaatgcatt agctagaact atattttttg gacaacgtgg   1980
agaatttaga gaacgtgctc tccaagacca gttacaaaga gctagtgcac taaacataat   2040
tattaacgct ataagtgtgt ggaacactgt atatatggaa aaagccgtag aagaattaaa   2100
agcaagagga gaatttagag aagatttaat gccatatgcg tggccgttag gatgggaaca   2160
tatcaatttt cttggagaat acaaatttga aggattacat gacactgggc aaatgaattt   2220
acgtccttta cgtataaaag agccgttta ttcttaatat aacggctctt tttatagaaa   2280
aaatccttag cgtggttttt ttccgaaatg ctggcggtac cccaagaatt agaaatgagt   2340
agatcaaatt attcacgaat agaatcagga aaatcagatc caaccataaa acactagaa    2400 caaattgcaa agtaactaa ctcaacgcta gtagtggatt taatcccaaa tgagccaaca    2460
gaaccagagc cagaaacaga atcagaacaa gtaacattgg atttagaaat ggaagaagaa   2520
aaaagcaatg acttcgtgtg aataatgcac gaaatcgttg cttattttt tttaaaagcg    2580 gtatactaga tataacgaaa caacgaactg aatagaaacg aaaaaagagc catgacacat   2640
ttataaaatg tttgacgaca ttttataaat gcatagcccg ataagattgc caaaccaacg   2700
cttatcagtt agtcagatga actcttccct cgtaagaagt tatttaatta actttgtttg   2760
```

-continued

```
aagacggtat ataaccgtac tatcattata tagggaaatc agagagtttt caagtatcta    2820
agctactgaa tttaagaatt gttaagcaat caatcggaaa tcgtttgatt gcttttttg      2880 tattcattta tagaaggtgg agtttgtatg aatcatgatg aatgtaaaac ttatataaaa     2940
aatagtttat tggagataag aaaattagca aatatctata cactagaaac gtttaagaaa    3000
gagttagaaa agagaaatat ctacttagaa acaaaatcag ataagtattt ttcttcggag    3060
ggggaagatt atatatataa gttaatagaa ataacaaaa taatttattc gattagtgga     3120
aaaaaattga cttataaagg aaaaaaatct ttttcaaaac atgcaatatt gaaacagttg    3180
aatgaaaaag caaaccaagt taattaaaca acctatttta taggatttat aggaaaggag    3240
aacagctgaa tgaatatccc ttttgttgta gaaactgtgc ttcatgacgg cttgttaaag    3300
tacaaattta aaatagtaa aattcgctca atcactacca agccaggtaa aagcaaaggg     3360
gctatttttg cgtatcgctc aaaatcaagc atgattggcg gtcgtggtgt tgttctgact    3420
tccgaggaag cgattcaaga aaatcaagat acatttacac attggacacc caacgtttat    3480
cgttatggaa cgtatgcaga cgaaaaccgt tcatacacga aaggacattc tgaaaacaat    3540
ttaagacaaa tcaataccct ctttattgat tttgatattc acacggcaaa agaaactatt    3600
tcagcaagcg atattttaac aaccgctatt gatttaggtt ttatgcctac tatgattatc    3660
aaatctgata aaggttatca agcatatttt gttttagaaa cgccagtcta tgtgacttca    3720
aaatcagaat ttaaatctgt caaagcagcc aaaataattt cgcaaaatat ccgagaatat    3780
tttggaaagt ctttgccagt tgatctaacg tgtaatcatt ttggtattgc tcgcatacca    3840
agaacggaca atgtagaatt ttttgatcct aattaccgtt attctttcaa agaatggcaa    3900
gattggtctt tcaaacaaac agataataag ggctttactc gttcaagtct aacggtttta    3960
agcggtacag aagcaaaaa acaagtagat gaaccctggt ttaatctctt attgcacgaa    4020
acgaaatttt caggagaaaa gggtttaata gggcgtaata acgtcatgtt taccctctct    4080
ttagcctact ttagttcagg ctattcaatc gaaacgtgcg aatataatat gtttgagttt    4140
aataatcgat tagatcaacc cttagaagaa aaagaagtaa tcaaaattgt tagaagtgcc    4200
tattcagaaa actatcaagg ggctaatagg gaatacatta ccattctttg caaagcttgg    4260
gtatcaagtg atttaaccag taagatttta tttgtccgtc aagggtggtt taaattcaag    4320
aaaaaaagaa gcgaacgtca acgtgttcat ttgtcagaat ggaaagaaga tttaatggct    4380
tatattagcg aaaaaagcga tgtatacaag cctattttag tgacgaccaa aaaagagatt    4440
agagaagtgc taggcattcc tgaacggaca ttagataaat tgctgaaggt actgaaggcg    4500
aatcaggaaa ttttctttaa gattaaacca ggaagaaatg gtggcattca acttgctagt    4560
gttaaatcat tgttgctatc gatcattaaa gtaaaaaaag aagaaaaga aagctatata    4620 aaggcgctga caaattcttt tgacttagag catacattca ttcaagagac tttaaacaag    4680
ctagcagaac gccctaaaac ggacacacaa ctcgatttgt ttagctatga tacaggctga    4740
aaataaaacc cgcactatgc cattacattt atatctatga tacgtgtttg tttttctttt    4800
gctgtttagc gaatgattag cagaaatata cagagtaaga ttttaattaa ttattagggg    4860
gagaaggaga gagtagcccg aaaacttttta gttggcttgg actgaacgaa gtgagggaaa   4920
ggctactaaa acgtcgaggg gcagtgagag cgaagcgaac acttgatttt ttaattttct    4980
atcttttata ggtcattaga gtatacttat ttgtcctata aactatttag cagcataata    5040
gatttattga ataggtcatt taagttgagc atattagagg aggaaaatct tggagaaata    5100
```

-continued

| | |
|---|---:|
| tttgaagaac cgattacat ggattggatt agttcttgtg gttacgtggt ttttaactaa | 5160 |
| aagtagtgaa ttttgattt ttggtgtgtg tgtcttgttg ttagtatttg ctagtcaaag | 5220 |
| tgattaaata | 5230 |

<210> SEQ ID NO 6
<211> LENGTH: 5906
<212> TYPE: DNA
<213> ORGANISM: Artificial Sequence
<220> FEATURE:
<223> OTHER INFORMATION: Description of Artificial Sequence: plamsid pT1NX

<400> SEQUENCE: 6

| | |
|---|---:|
| gaattcgatt aagtcatctt acctctttta ttagtttttt cttataatct aatgataaca | 60 |
| tttttataat taatctataa accatatccc tctttggaat caaaatttat tatctactcc | 120 |
| tttgtagata tgttataata caagtatcag atctgggaga ccacaacggt ttcccactag | 180 |
| aaataatttt gtttaacttt agaaggaga tatacgcatg aaaaaaaga ttatctcagc | 240 |
| tatttaatg tctacagtca tactttctgc tgcagcccg ttgtcaggtg tttacgccgg | 300 |
| cgacggatcc aaaagaggaa gacaataaca agcctggcaa agaagacaat aacaagcctg | 360 |
| gcaaagaaga caataacaag cctggcaaag aagacaacaa caagcctggc aaagaagaca | 420 |
| acaacaagcc tggtaaagaa gacaacaaca gcctggcaa agaagacggc aacaagcctg | 480 |
| gtaaagaaga caacaaaaaa cctggtaaag aagatgcaa caagcctggt aaagaagaca | 540 |
| acaaaaaacc tggtaaagaa gacggcaaca gcctggcaa agaagatggc aacaaacctg | 600 |
| gtaaagaaga tggtaacgga gtacatgtcg ttaaacctgg tgatacagta aatgacattg | 660 |
| caaaagcaaa cggcactact gctgacaaaa ttgctgcaga taacaaatta gctgataaaa | 720 |
| acatgatcaa acctggtcaa gaacttgttg ttgataagaa gcaaccagca aaccatgcag | 780 |
| atgctaacaa agctcaagca ttaccagaaa ctggcgaaga aaatccattc atcggtacaa | 840 |
| ctgtatttgg tggattatca ttagcctag gtgcagcgtt attagctgga cgtcgtcgcg | 900 |
| aactataact agtagatccg gctgctaaca agcccgaaa ggaagctgag ttggctgctg | 960 |
| ccaccgctga gcaataacta gcataacccc ttggggcctc taaacgggtc ttgaggggtt | 1020 |
| ttttgctgaa aggaggaact atatccggat gacctgcagg caagctctag aatcgatacg | 1080 |
| attttgaagt ggcaacagat aaaaaaaagc agtttaaaat tgttgctgaa cttttaaaac | 1140 |
| aagcaaatac aatcattgtc gcaacagata gcgacagaga aggcgaaaac attgcctggt | 1200 |
| cgatcattca taaagcaaat gccttttcta aagataaaac gtataaagaa ctatggatca | 1260 |
| atagtttaga aaaagatgtg atccgtagcg gttttcaaaa tttgcaacca ggaatgaatt | 1320 |
| actatccctt ttatcaagaa gcgcaaaaga aaacgaaat gatacaccaa tcagtgcaaa | 1380 |
| aaagatata atgggagata agacggttcg tgttcgtgct gacttgcacc atatcataaa | 1440 |
| aatcgaaaca gcaaagaatg gcggaaacgt aaagaagtt atggaaataa gacttagaag | 1500 |
| caaacttaag agtgtgttga tagtgcagta tcttaaaatt ttgtataata ggaattgaag | 1560 |
| ttaaattaga tgctaaaaat ttgtaattaa gaaggagtga ttacatgaac aaaaatataa | 1620 |
| aatattctca aaactttta acgagtgaaa agtactcaa ccaaataata aaacaattga | 1680 |
| atttaaaaga aaccgatacc gtttacgaaa ttggaacagg taaagggcat ttaacgacga | 1740 |
| aactggctaa aataagtaaa caggtaacgt ctattgaatt agacagtcat ctattcaact | 1800 |
| tatcgtcaga aaaattaaaa ctgaatactc gtgtcacttt aattcaccaa gatattctac | 1860 |

```
agtttcaatt ccctaacaaa cagaggtata aaattgttgg gagtattcct taccatttaa    1920
gcacacaaat tattaaaaaa gtggttttgg aaagccatgc gtctgacatc tatctgattg    1980
ttgaagaagg attctacaag cgtaccttgg atattcaccg aacactaggg ttgctcttgc    2040
acactcaagt ctcgattcag caattgctta agctgccagc ggaatgcttt catcctaaac    2100
caaaagtaaa cagtgtctta ataaaactta cccgccatac cacagatgtt ccagataaat    2160
attggaagct atatacgtac tttgtttcaa aatgggtcaa tcgagaatat cgtcaactgt    2220
ttactaaaaa tcagtttcat caagcaatga aacacgccaa agtaaacaat ttaagtaccg    2280
ttacttatga gcaagtattg tctatttttta atagttatct attatttaac gggaggaaat    2340
aattctatga gtcgcttttg taaatttgga agttacacg ttactaaagg gaatgtagat    2400
aaattattag gtatactact gacagcttcc aaggagctaa agaggtccct agcgctctta    2460
tcatggggaa gctcggatca tatgcaagac aaaataaact cgcaacagca cttggagaaa    2520
tgggacgaat cgagaaaacc ctctttacgc tggattacat atctaataaa gccgtaagga    2580
gacgggttca aaaggttta aataaaggag aagcaatcaa tgcattagct agaactatat    2640 ttttttggaca acgtggagaa tttagagaac gtgctctcca agaccagtta caaagagcta    2700
gtgcactaaa cataattatt aacgctataa gtgtgtggaa cactgtatat atggaaaaag    2760
ccgtagaaga attaaaagca agaggagaat ttagagaaga tttaatgcca tatgcgtggc    2820
cgttaggatg ggaacatatc aattttcttg gagaatacaa atttgaagga ttacatgaca    2880
ctgggcaaat gaatttacgt cctttacgta taaaagagcc gttttattct taatataacg    2940
gctcttttta tagaaaaaat ccttagcgtg gtttttttcc gaaatgctgg cggtaccca    3000 agaattagaa atgagtagat caaattattc acgaatagaa tcaggaaaat cagatccaac    3060
cataaaaaca ctagaacaaa ttgcaaagtt aactaactca acgctagtag tggatttaat    3120
cccaaatgag ccaacagaac cagagccaga aacagaatca gaacaagtaa cattggattt    3180
agaaatggaa gaagaaaaaa gcaatgactt cgtgtgaata atgcacgaaa tcgttgctta    3240
ttttttttta aagcggtat actagatata acgaaacaac gaactgaata gaaacgaaaa    3300
aagagccatg acacatttat aaaatgtttg acgacatttt ataaatgcat agcccgataa    3360
gattgccaaa ccaacgctta tcagttagtc agatgaactc ttccctcgta agaagttat    3420 taattaactt tgtttgaaga cggtatataa ccgtactatc attatatagg gaaatcagag    3480
agttttcaag tatctaagct actgaattta agaattgtta agcaatcaat cggaaatcgt    3540
ttgattgctt tttttgtatt catttataga aggtggagtt tgtatgaatc atgatgaatg    3600
taaaacttat ataaaaaata gtttattgga gataagaaaa ttagcaaata tctatacact    3660
agaaacgttt aagaaagagt tagaaaagag aaatatctac ttagaaacaa aatcagataa    3720 gtattttttct tcggaggggg aagattatat atataagtta atagaaaata acaaaataat    3780
ttattcgatt agtggaaaaa aattgactta taaggaaaaa aaatcttttt caaaacatgc    3840
aatattgaaa cagttgaatg aaaaagcaaa ccaagttaat taaacaacct attttatagg    3900
atttatagga aaggagaaca gctgaatgaa tatcccttttt gttgtagaaa ctgtgcttca    3960
tgacggcttg ttaaagtaca aatttaaaaa tagtaaaatt cgctcaatca ctaccaagcc    4020
aggtaaaagc aaagggggcta tttttgcgta tcgctcaaaa tcaagcatga ttggcggtcg    4080
tggtgttgtt ctgacttccg aggaagcgat tcaagaaaat caagatacat ttacacattg    4140
gacacccaac gtttatcgtt atggaacgta tgcagacgaa aaccgttcat acacgaaagg    4200
acattctgaa aacaatttaa gacaaatcaa taccttctttt attgattttg atattcacac    4260
```

-continued

```
ggcaaaagaa actatttcag caagcgatat tttaacaacc gctattgatt taggttttat      4320
gcctactatg attatcaaat ctgataaagg ttatcaagca tattttgttt tagaaacgcc      4380
agtctatgtg acttcaaaat cagaatttaa atctgtcaaa gcagccaaaa taatttcgca      4440
aaatatccga gaatattttg gaaagtcttt gccagttgat ctaacgtgta atcattttgg      4500
tattgctcgc ataccaagaa cggacaatgt agaattttt gatcctaatt accgttattc       4560
tttcaaagaa tggcaagatt ggtctttcaa acaaacagat aataagggct ttactcgttc      4620
aagtctaacg gttttaagcg gtacagaagg caaaaaaca gtagatgaac cctggtttaa       4680
tctcttattg cacgaaacga aattttcagg agaaagggt ttaatagggc gtaataacgt       4740
catgtttacc ctctctttag cctactttag ttcaggctat tcaatcgaaa cgtgcgaata     4800
taatatgttt gagtttaata atcgattaga tcaacccctta gaagaaaag aagtaatcaa     4860 aattgttaga agtgcctatt cagaaaacta tcaaggggct aatagggaat acattaccat     4920
tctttgcaaa gcttgggtat caagtgattt aaccagtaaa gatttatttg tccgtcaagg     4980
gtggtttaaa ttcaagaaaa aaagaagcga acgtcaacgt gttcatttgt cagaatggaa     5040
agaagattta atggcttata ttagcgaaaa aagcgatgta tacaagcctt atttagtgac     5100
gaccaaaaaa gagattagag aagtgctagg cattcctgaa cggacattag ataaattgct     5160
gaaggtactg aaggcgaatc aggaaatttt ctttaagatt aaaccaggaa gaaatggtgg     5220
cattcaactt gctagtgtta aatcattgtt gctatcgatc attaaagtaa aaaagaaga     5280 aaagaaagc tatataaagg cgctgacaaa ttcttttgac ttagagcata cattcattca      5340
agagacttta aacaagctag cagaacgccc taaaacggac acacaactcg atttgtttag     5400
ctatgataca ggctgaaaat aaaacccgca ctatgccatt acatttatat ctatgatacg     5460 tgtttgttt tcttgctg tttagcgaat gattagcaga aatatacaga gtaagatttt        5520
aattaattat taggggaga aggagagagt agcccgaaaa cttttagttg gcttggactg      5580
aacgaagtga gggaaaggct actaaaacgt cgaggggcag tgagagcgaa gcgaacactt     5640
gattttttaa ttttctatct tttataggtc attagagtat acttatttgt cctataaact     5700
atttagcagc ataatagatt tattgaatag gtcatttaag ttgagcatat tagaggagga    5760
aaatcttgga gaaatatttg aagaacccga ttacatggat tggattagtt cttgtggtta    5820
cgtggttttt aactaaaagt agtgaatttt tgatttttgg tgtgtgtgtc ttgttgttag    5880
tatttgctag tcaaagtgat taaata                                         5906
```

<210> SEQ ID NO 7
<211> LENGTH: 5770
<212> TYPE: DNA
<213> ORGANISM: Artificial Sequence
<220> FEATURE:
<223> OTHER INFORMATION: Description of Artificial Sequence: plasmid pT1MIL10

<400> SEQUENCE: 7

```
gaattcgatt aagtcatctt acctcttta ttagtttttt cttataatct aatgataaca       60
tttttataat taatctataa accatatccc tctttggaat caaaatttat tatctactcc      120
tttgtagata tgttataata caagtatcag atctgggaga ccacaacggt ttcccactag      180
aaataatttt gtttaacttt agaaaggaga tatacgcatg aaaaaaaaga ttatctcagc      240 tatttaatg tctacagtca tactttctgc tgcagccccg ttgtcaggtg tttacgccca       300
gtacagccgg gaagacaata actgcaccca cttcccagtc ggccagagcc acatgctcct      360
```

```
agagctgcgg actgccttca gccaggtgaa gactttcttt caaacaaagg accagctgga    420
caacatactg ctaaccgact ccttaatgca ggactttaag ggttacttgg gttgccaagc    480
cttatcggaa atgatccagt tttacctggt agaagtgatg ccccaggcag agaagcatgg    540
cccagaaatc aaggagcatt tgaattccct gggtgagaag ctgaagaccc tcaggatgcg    600
gctgaggcgc tgtcatcgat ttctcccctg tgaaaataag agcaaggcag tggagcaggt    660
gaagagtgat tttaataagc tccaagacca aggtgtctac aaggccatga atgaatttga    720
catcttcatc aactgcatag aagcatacat gatgatcaaa atgaaaagct aactagtaga    780
tccggctgct aacaaagccc gaaaggaagc tgagttggct gctgccaccg ctgagcaata    840
actagcataa cccttgggg cctctaaacg ggtcttgagg ggttttttgc tgaaaggagg    900
aactatatcc ggatgacctg caggcaagct ctagaatcga tacgattttg aagtggcaac    960
agataaaaaa aagcagttta aaattgttgc tgaactttta aaacaagcaa atacaatcat   1020
tgtcgcaaca gatagcgaca gagaaggcga aaacattgcc tggtcgatca ttcataaagc   1080
aaatgccttt tctaaagata aaacgtataa agactatgg atcaatagtt tagaaaaaga   1140
tgtgatccgt agcggttttc aaaatttgca accaggaatg aattactatc ccttttatca   1200
agaagcgcaa aagaaaaacg aaatgataca ccaatcagtg caaaaaaga tataatggga   1260 gataagacgg ttcgtgttcg tgctgacttg caccatatca taaaaatcga acagcaaag   1320 aatggcggaa acgtaaaaga agttatgaa ataagactta aagcaaact taagagtgtg   1380 ttgatagtgc agtatcttaa aattttgtat aataggaatt gaagttaaat tagatgctaa   1440
aaatttgtaa ttaagaagga gtgattacat gaacaaaaat ataaaatatt ctcaaaactt   1500
tttaacgagt gaaaaagtac tcaaccaaat aataaaacaa ttgaatttaa agaaaccga   1560 taccgtttac gaaattggaa caggtaaagg gcatttaacg acgaaactgg ctaaaataag   1620
taaacaggta acgtctattg aattagacag tcatctattc aacttatcgt cagaaaaatt   1680
aaaactgaat actcgtgtca ctttaattca ccaagatatt ctacagtttc aattccctaa   1740
caaacagagg tataaaattg ttgggagtat tccttaccat ttaagcacac aaattattaa   1800
aaaagtggtt tttgaaagcc atgcgtctga catctatctg attgttgaag aaggattcta   1860
caagcgtacc ttggatattc accgaacact agggttgctc ttgcacactc aagtctcgat   1920
tcagcaattg cttaagctgc agcggaatg ctttcatcct aaaccaaaag taaacagtgt   1980
cttaataaaa cttacccgcc ataccacaga tgttccagat aaatattgga agctatatac   2040
gtactttgtt tcaaaatggg tcaatcgaga atatcgtcaa ctgtttacta aaaatcagtt   2100
tcatcaagca atgaaacacg ccaaagtaaa caatttaagt accgttactt atgagcaagt   2160
attgtctatt tttaatagtt atctattatt taacgggagg aaataattct atgagtcgct   2220
tttgtaaatt tggaaagtta cacgttacta agggaatgt agataaatta ttaggtatac   2280
tactgacagc ttccaaggag ctaaagaggt ccctagcgct cttatcatgg ggaagctcgg   2340
atcatatgca agacaaaata aactcgcaac agcacttgga gaaatgggac gaatcgagaa   2400
aaccctcttt acgctggatt acatatctaa taagccgta aggagacggg ttcaaaaagg   2460
tttaaataaa ggagaagcaa tcaatgcatt agctagaact atatttttg gacaacgtgg   2520 agaatttaga gaacgtgctc tccaagacca gttacaaaga gctagtgcac taaacataat   2580
tattaacgct ataagtgtgt ggaacactgt atatatgaa aaagccgtag aagaattaaa   2640
agcaagagga gaatttagag aagatttaat gccatatgcg tggccgttag gatgggaaca   2700
```

```
tatcaatttt cttggagaat acaaatttga aggattacat gacactgggc aaatgaattt    2760
acgtccttta cgtataaaag agccgtttta ttcttaatat aacggctctt tttatagaaa    2820
aaatccttag cgtggttttt ttccgaaatg ctggcggtac cccaagaatt agaaatgagt    2880
agatcaaatt attcacgaat agaatcagga aaatcagatc caaccataaa acactagaa     2940 caaattgcaa agttaactaa ctcaacgcta gtagtgcatt taatcccaaa tgagccaaca    3000
gaaccagagc cagaaacaga atcagaacaa gtaacattgg atttagaaat ggaagaagaa    3060
aaaagcaatg acttcgtgtg aataatgcac gaaatcgttg cttattttt tttaaaagcg    3120 gtatactaga tataacgaaa caacgaactg aatagaaacg aaaaaagagc catgacacat    3180
ttataaaatg tttgacgaca ttttataaat gcatagcccg ataagattgc caaccaacg    3240 cttatcagtt agtcagatga actcttccct cgtaagaagt tatttaatta actttgtttg    3300
aagacggtat ataaccgtac tatcattata tagggaaatc agagagtttt caagtatcta    3360
agctactgaa tttaagaatt gttaagcaat caatcggaaa tcgtttgatt gcttttttg     3420 tattcattta tagaaggtgg agtttgtatg aatcatgatg aatgtaaaac ttatataaaa    3480
aatagtttat tggagataag aaaattagca aatatctata cactagaaac gtttaagaaa    3540
gagttagaaa agagaaatat ctacttagaa acaaaatcag ataagtattt ttcttcggag    3600
ggggaagatt atatatataa gttaatagaa aataacaaaa taatttattc gattagtgga    3660
aaaaaattga cttataaagg aaaaaatct ttttcaaaac atgcaatatt gaaacagttg     3720
aatgaaaaag caaccaagt taattaaaca acctatttta taggatttat aggaaaggag     3780
aacagctgaa tgaatatccc ttttgttgta gaaactgtgc ttcatgacgg cttgttaaag    3840
tacaaattta aaaatagtaa aattcgctca atcactacca agccaggtaa aagcaaaggg    3900 gctattttg cgtatcgctc aaaatcaagc atgattggcg gtcgtggtgt tgttctgact     3960
tccgaggaag cgattcaaga aaatcaagat acatttacac attggacacc caacgtttat    4020
cgttatggaa cgtatgcaga cgaaaaccgt tcatacacga aaggacattc tgaaaacaat    4080
ttaagacaaa tcaatacctt ctttattgat tttgatattc acacggcaaa agaaactatt    4140
tcagcaagcg atattttaac aaccgctatt gatttaggtt ttatgcctac tatgattatc    4200
aaatctgata aaggttatca agcatatttt gttttagaaa cgccagtcta tgtgacttca    4260
aaatcagaat ttaaatctgt caaagcagcc aaaataattt cgcaaaatat ccgagaatat    4320 tttgaaagt ctttgccagt tgatctaacg tgtaatcatt ttggtattgc tcgcatacca    4380
agaacggaca atgtagaatt ttttgatcct aattaccgtt attctttcaa agaatggcaa    4440
gattggtctt tcaaacaaac agataataag ggctttactc gttcaagtct aacggtttta    4500
agcggtacag aaggcaaaaa acaagtagat gaaccctggt ttaatctctt attgcacgaa    4560 acgaaattt caggagaaaa gggtttaata gggcgtaata acgtcatgtt taccctctct    4620
ttagcctact ttagttcagg ctattcaatc gaaacgtgcg aatataatat gtttgagttt    4680
aataatcgat tagatcaacc cttagaagaa aagaagtaa tcaaaattgt tagaagtgcc     4740
tattcagaaa actatcaagg ggctaatagg gaatacatta ccattctttg caaagcttgg    4800
gtatcaagtg atttaaccag taaagattta tttgtccgtc aagggtggtt taaattcaag    4860 aaaaaagaa gcgaacgtca acgtgttcat tgtcagaat ggaaagaaga tttaatggct      4920
tatattagcg aaaaaagcga tgtatacaag ccttatttag tgacgaccaa aaaagagatt    4980
agagaagtgc taggcattcc tgaacggaca ttagataaat tgctgaaggt actgaaggcg    5040
aatcaggaaa ttttctttaa gattaaacca ggaagaaatg gtggcattca acttgctagt    5100
```

```
gttaaatcat tgttgctatc gatcattaaa gtaaaaaag  aagaaaaaga aagctatata      5160
aaggcgctga caaattcttt tgacttagag catacattca ttcaagagac tttaaacaag      5220
ctagcagaac gccctaaaac ggacacacaa ctcgatttgt ttagctatga tacaggctga      5280
aaataaaacc cgcactatgc cattacattt atatctatga tacgtgtttg ttttttcttt      5340
gctgtttagc gaatgattag cagaaatata cagagtaaga ttttaattaa ttattagggg      5400
gagaaggaga gagtagcccg aaaacttttt gttggcttgg actgaacgaa gtgagggaaa      5460
ggctactaaa acgtcgaggg gcagtgagag cgaagcgaac acttgatttt ttaattttct      5520 atctttata  ggtcattaga gtatacttat ttgtcctata aactatttag cagcataata      5580
gatttattga ataggtcatt taagttgagc atattagagg aggaaaatct tggagaaata      5640
tttgaagaac ccgattacat ggattggatt agttcttgtg gttacgtggt ttttaactaa      5700
aagtagtgaa ttttgatttt ttggtgtgtg tgtcttgttg ttagtatttg ctagtcaaag      5760
tgattaaata                                                            5770

<210> SEQ ID NO 8
<211> LENGTH: 5870
<212> TYPE: DNA
<213> ORGANISM: Artificial Sequence
<220> FEATURE:
<223> OTHER INFORMATION: Description of Artificial Sequence: plasmid
      pT1TR5AH

<400> SEQUENCE: 8
gaattcgatt aagtcatctt acctctttta ttagttttttt cttataatct aatgataaca      60
tttttataat taatctataa accatatccc tctttggaat caaatttat  tatctactcc      120 tttgtagata tgttataata caagtatcag atctgggaga ccacaacggt ttcccactag      180
aaataatttt gtttaacttt agaaggaga  tatacgcatg aaaaaaaaga ttatctcagc      240
tattttaatg tctacagtca tactttctgc tgcagccccg ttgtcaggtg tttacgccct      300
ggtcccttct cttggtgacc gggagaagag ggatagcttg tgtccccaag gaaagtatgt      360
ccattctaag aacaattcca tctgctgcac caagtgccac aaaggaacct acttggtgag      420
tgactgtccg agcccagggc gggatacagt ctgcagggag tgtgaaaagg gcacctttac      480
ggcttcccag aattacctca ggcagtgtct cagttgcaag acatgtcgga agaaatgtc       540 ccaggtggag atctctcctt gccaagctga caaggacacg tgtgtggct  gtaaggagaa      600 ccagttccaa cgctacctga gtgagacaca cttccagtgc gtggactgca gcccctgctt      660
caacggcacc gtgacaatcc cctgtaagga gactcagaac accgtgtgta actgccatgc      720 agggttctt  ctgagagaaa gtgagtgcgt cccttgcagc cactgcaaga aaatgagga       780 gtgtatgaag ttgtgcctac ctcctccgct tgcaaatgtc acaaaccccc aggactcagg      840
tactgcgcat catcatcatc atcattaata gactagtaga tccggctgct aacaaagccc      900
gaaaggaagc tgagttggct gctgccaccg ctgagcaata actagcataa ccccttgggg      960
cctctaaacg ggtcttgagg ggttttttgc tgaaggagg  aactatatcc ggatgacctg     1020
caggcaagct ctagaatcga tacgattttg aagtggcaac agataaaaaa aagcagttta     1080
aaattgttgc tgaacttttta aaacaagcaa atacaatcat tgtcgcaaca gatagcgaca     1140
gagaaggcga aaacattgcc tggtcgatca ttcataaagc aaatgccttt tctaaagata     1200
aaacgtataa aagactatgg atcaatagtt tagaaaaaga tgtgatccgt agcggttttc     1260
aaaatttgca accaggaatg aattactatc cctttttatca agaagcgcaa aagaaaaacg     1320
```

-continued

```
aaatgataca ccaatcagtg caaaaaaaga tataatggga gataagacgg ttcgtgttcg    1380
tgctgacttg caccatatca taaaaatcga aacagcaaag aatggcggaa acgtaaaaga    1440
agttatggaa ataagactta gaagcaaact taagagtgtg ttgatagtgc agtatcttaa    1500
aattttgtat aataggaatt gaagttaaat tagatgctaa aaatttgtaa ttaagaagga    1560
gtgattacat gaacaaaaat ataaaatatt ctcaaaactt tttaacgagt gaaaaagtac    1620
tcaaccaaat aataaaacaa ttgaatttaa agaaaccga taccgtttac gaaattggaa    1680
caggtaaagg gcatttaacg acgaaactgg ctaaataag taaacaggta acgtctattg    1740
aattagacag tcatctattc aacttatcgt cagaaaaatt aaaactgaat actcgtgtca    1800
ctttaattca ccaagatatt ctacagtttc aattccctaa caaacagagg tataaaattg    1860
ttgggagtat tccttaccat ttaagcacac aaattattaa aaaagtggtt tttgaaagcc    1920
atgcgtctga catctatctg attgttgaag aaggattcta caagcgtacc ttggatattc    1980
accgaacact agggttgctc ttgcacactc aagtctcgat tcagcaattg cttaagctgc    2040
cagcggaatg ctttcatcct aaaccaaaag taaacagtgt cttaataaaa cttacccgcc    2100
ataccacaga tgttccagat aaatattgga agctatatac gtactttgtt tcaaaatggg    2160
tcaatcgaga atatcgtcaa ctgtttacta aaaatcagtt tcatcaagca atgaaacacg    2220
ccaaagtaaa caatttaagt accgttactt atgagcaagt attgtctatt tttaatagtt    2280
atctattatt taacgggagg aaataattct atgagtcgct tttgtaaatt tggaaagtta    2340
cacgttacta aagggaatgt agataaatta ttaggtatac tactgacagc ttccaaggag    2400
ctaaagaggt ccctagcgct cttatcatgg ggaagctcgg atcatatgca agacaaaata    2460
aactcgcaac agcacttgga gaaatgggac gaatcgagaa aaccctcttt acgctggatt    2520
acatatctaa taaagccgta aggagacggg ttcaaaaagg tttaaataaa ggagaagcaa    2580
tcaatgcatt agctagaact atattttttg gacaacgtgg agaatttaga gaacgtgctc    2640
tccaagacca gttacaaaga gctagtgcac taaacataat tattaacgct ataagtgtgt    2700
ggaacactgt atatatggaa aaagccgtag aagaattaaa agcaagagga gaatttagag    2760
aagatttaat gccatatgcg tggccgttag gatgggaaca tatcaatttt cttggagaat    2820
acaaatttga aggattacat gacactgggc aaatgaattt acgtccttta cgtataaaag    2880
agccgtttta ttcttaatat aacggctctt tttatagaaa aaatccttag cgtggttttt    2940
ttccgaaatg ctggcggtac cccaagaatt agaaatgagt agatcaaatt attcacgaat    3000
agaatcagga aaatcagatc caaccataaa aacactagaa caaattgcaa agttaactaa    3060
ctcaacgcta gtagtggatt taatcccaaa tgagccaaca gaaccagagc cagaaacaga    3120
atcagaacaa gtaacattgg atttagaaat ggaagaagaa aaaagcaatg acttcgtgtg    3180
aataatgcac gaaatcgttg ctattttttt tttaaaagcg gtatactaga tataacgaaa    3240
caacgaactg aatagaaacg aaaaagagc catgacacat ttataaaatg tttgacgaca    3300
ttttataaat gcatagcccg ataagattgc caaccaacg cttatcagtt agtcagatga    3360
actcttccct cgtaagaagt tatttaatta actttgtttg aagacggtat ataaccgtac    3420
tatcattata tagggaaatc agagagtttt caagtatcta agctactgaa tttaagaatt    3480
gttaagcaat caatcggaaa tcgtttgatt gcttttttg tattcattta tagaaggtgg    3540
agtttgtatg aatcatgatg aatgtaaaac ttatataaaa aatagtttat tggagataag    3600
aaaattagca aatatctata cactagaaac gtttaagaaa gagttagaaa agagaaatat    3660
```

-continued

```
ctacttagaa acaaaatcag ataagtattt ttcttcggag ggggaagatt atatatataa    3720
gttaatagaa aataacaaaa taatttattc gattagtgga aaaaaattga cttataaagg    3780
aaaaaaatct ttttcaaaac atgcaatatt gaaacagttg aatgaaaaag caaaccaagt    3840
taattaaaca acctatttta taggatttat aggaaaggag aacagctgaa tgaatatccc    3900
ttttgttgta gaaactgtgc ttcatgacgg cttgttaaag tacaaattta aaaatagtaa    3960
aattcgctca atcactacca agccaggtaa aagcaaaggg gctattttg cgtatcgctc     4020
aaaatcaagc atgattggcg gtcgtggtgt tgttctgact tccgaggaag cgattcaaga    4080
aaatcaagat acatttacac attggacacc caacgtttat cgttatggaa cgtatgcaga    4140
cgaaaaccgt tcatacacga aaggacattc tgaaaacaat ttaagacaaa tcaataccct    4200
ctttattgat tttgatattc acacggcaaa agaaactatt tcagcaagcg atattttaac    4260
aaccgctatt gatttaggtt ttatgcctac tatgattatc aaatctgata aaggttatca    4320
agcatatttt gttttagaaa cgccagtcta tgtgacttca aaatcagaat ttaaatctgt    4380
caaagcagcc aaaataattt cgcaaaatat ccgagaatat tttggaaagt ctttgccagt    4440
tgatctaacg tgtaatcatt tggtattgc tcgcatacca agaacggaca atgtagaatt      4500
ttttgatcct aattaccgtt attctttcaa agaatggcaa gattggtctt tcaaacaaac    4560
agataataag ggctttactc gttcaagtct aacggttta agcggtacag aaggcaaaaa     4620
acaagtagat gaaccctggt ttaatctctt attgcacgaa acgaaatttt caggagaaaa    4680
gggtttaata gggcgtaata acgtcatgtt tacctctct ttagcctact ttagttcagg      4740
ctattcaatc gaaacgtgcg aatataatat gtttgagttt aataatcgat tagatcaacc    4800
cttagaagaa aaagaagtaa tcaaaattgt tagaagtgcc tattcagaaa actatcaagg    4860
ggctaatagg gaatacatta ccattctttg caaagcttgg gtatcaagtg atttaaccag    4920
taaagattta tttgtccgtc aagggtggtt taaattcaag aaaaaaagaa gcgaacgtca    4980
acgtgttcat ttgtcagaat ggaaagaaga tttaatggct tatattagcg aaaaaagcga    5040
tgtatacaag ccttatttag tgacgaccaa aaaagagatt agagaagtgc taggcattcc    5100
tgaacggaca ttagataaat tgctgaaggt actgaaggcg aatcaggaaa ttttctttaa    5160
gattaaacca ggaagaaatg gtggcattca acttgctagt gttaaatcat tgttgctatc    5220
gatcattaaa gtaaaaaaag aagaaaaga aagctatata aaggcgctga caaattcttt    5280
tgacttagag catacattca ttcaagagac tttaaacaag ctagcagaac gccctaaaac    5340
ggacacacaa ctcgatttgt ttagctatga tacaggctga aaataaaacc cgcactatgc    5400
cattacattt atatctatga tacgtgtttg ttttttcttt gctgtttagc gaatgattag    5460
cagaaatata cagagtaaga ttttaattaa ttattagggg gagaaggaga gagtagcccg    5520
aaaacttta gttggcttgg actgaacgaa gtgagggaaa ggctactaaa acgtcgaggg      5580
gcagtgagag cgaagcgaac acttgatttt ttaattttct atcttttata ggtcattaga    5640
gtatacttat ttgtcctata aactatttag cagcataata gatttattga ataggtcatt    5700
taagttgagc atattagagg aggaaaatct tggagaaata tttgaagaac ccgattacat    5760
ggattggatt agttcttgtg gttacgtggt ttttaactaa aagtagtgaa tttttgattt    5820
ttggtgtgtg tgtcttgttg ttagtatttg ctagtcaaag tgattaaata               5870
```